United States Patent
Banin et al.

(10) Patent No.: US 12,290,576 B2
(45) Date of Patent: *May 6, 2025

(54) MANUFACTURING OF DIMERIC CONTRAST AGENTS

(71) Applicant: BRACCO IMAGING S.P.A., Milan (IT)

(72) Inventors: Andrea Banin, Collegno (IT); Andrea Barale, Bibiana (IT); Valeria Boi, Strambino (IT); Sonia Gazzetto, Cascinette d'Ivrea (IT); Federica Buonsanti, Turin (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/565,770

(22) PCT Filed: Jul. 26, 2022

(86) PCT No.: PCT/EP2022/070901
§ 371 (c)(1),
(2) Date: Nov. 30, 2023

(87) PCT Pub. No.: WO2023/006721
PCT Pub. Date: Feb. 2, 2023

(65) Prior Publication Data
US 2024/0269330 A1    Aug. 15, 2024

(30) Foreign Application Priority Data
Jul. 27, 2021   (EP) .................... 21187883

(51) Int. Cl.
*A61B 5/055*   (2006.01)
*A61K 49/10*   (2006.01)

(52) U.S. Cl.
CPC .................. *A61K 49/106* (2013.01)

(58) Field of Classification Search
CPC .. A61K 49/106; A61K 49/122; C07D 257/02; C07F 5/003
See application file for complete search history.

(56) References Cited

U.S. PATENT DOCUMENTS 10,407,412 B2 *  9/2019  Boi .................. C07D 257/02
2018/0362511 A1   12/2018 Boi et al.

FOREIGN PATENT DOCUMENTS

| JP | 4733271 B2 * | 7/2011 | ........... A61K 49/085 |
| WO | 2017098044 A1 | 6/2017 | |
| WO | WO-2021116165 A1 * | 6/2021 | ........... C07D 257/02 |

OTHER PUBLICATIONS

Kumar et al. (Anal. Chem. 1994, 66, 295-299).*
Ersoy et al. (J. Magn. Reson. Imaging 2007; 26, 1190-1197).*
Green, T.W., et al., "Protection for the Amino Group," In: Protective Groups in Organic Synthesis, third edition, John Wiley & Sons, N.Y. (1999).
International Search Report and Written Opinion for PCT/EP2022/070901, mailed Oct. 28, 2022.
Moore, D.A., "Selective Trialkylation of Cyclen With tert-Butyl Bromoacetate [1,4,7,10-Tetraazacyclododecane-1,4,7-triacetic acid, Tri-tert-butyl Ester Hydrobromide]," Org. Synth., 85:10-14 (2008).

* cited by examiner

*Primary Examiner* — Michael G. Hartley
*Assistant Examiner* — Melissa J Perreira
(74) *Attorney, Agent, or Firm* — VIVICAR Law, PLLC

(57) ABSTRACT

The invention relates to a process for the preparation of dimeric contrast agents for use in Magnetic resonance Imaging (MRI), in particular [μ-[1-[bis[2-(hydroxy-κO)-3-[4,7,10-tris[(carboxy-κO)methyl]-1,4,7,10-tetraazacyclododec-1-yl-κ$N^1$,κ$N^4$,κ$N^7$,κ$N^{10}$]propyl]amino]-1-deoxy-D-glucitolate(6-)]]di-gadolinium complex, which includes preparation steps carried out one-pot (without isolation of the obtained intermediate) and precipitation of at least part of free gadolinium metal ions in excess.

42 Claims, No Drawings

MANUFACTURING OF DIMERIC CONTRAST AGENTS

CROSS-REFERENCE TO RELATED APPLICATIONS

This application is the national stage application of corresponding international application number PCT/EP2022/070901, filed Jul. 26, 2022, which claims priority to and the benefit of European application no. 21187883.0, filed Jul. 27, 2021, which is hereby incorporated by reference in its entirety.

FIELD OF THE INVENTION

The present invention relates to the preparation of contrast agents for use in Magnetic Resonance Imaging (MRI). In particular the invention relates to a new process for the preparation of dimeric contrast agents, especially [μ-[1-[bis [2-(hydroxy-κO)-3-[4,7,10-tris[(carboxy-κO)methyl]-1,4,7,10-tetraazacyclododec-1-yl-κ$N^1$, κ$N^4$, κ$N^7$, κ$N^{10}$]propyl] amino]-1-deoxy-D-glucitolato(6-)]]di-Gadolinium complex (Compound 5).

STATE OF THE ART

Magnetic Resonance Imaging (MRI) is a renowned diagnostic imaging technique increasingly used in clinical diagnostics for a growing number of indications.

Contrast agents for use in the MRI imaging technique typically include a paramagnetic metal ion which is complexed with a cyclic or acyclic chelating ligand, more typically a polyaminopolycarboxylic chelator. The most important class of MRI contrast agents is represented by the Gd(III) chelates which are currently used in about ⅓ of the clinical tests. Indeed, Gd(III) is highly paramagnetic with seven unpaired electrons and a long electronic relaxation time, making it an excellent candidate as a relaxation agent. However, the gadolinium metal ion $[Gd(H_2O)_8]^{3+}$ is toxic for living organism even at low doses (10-20 micromol/kg).

Thus, in order to be considered as a potentially valuable MRI contrast agent, a Gd(III) complex shall display a high thermodynamic (and possibly kinetic) stability in to prevent the release of the toxic metal ion. Moreover, processes for manufacturing the Gd(III) complex are advantageous when they allow effective and efficient removal of the toxic metal ion that is present within the reaction mixture after the complexation step.

WO 2017/098044 (same applicant as the present application) discloses dimeric paramagnetic complexes useful as contrast agents, specifically in Magnetic Resonance Imaging (MRI), of formula

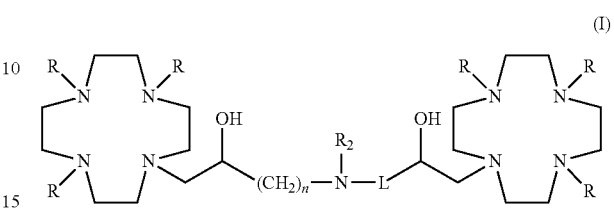

and a synthetic route for their preparation.

Among a number of specific compounds, the application discloses the di-gadolinium complex of the 1-[bis[2-hydroxy-3-[4,7,10-tris(carboxymethyl)-1,4,7,10-tetraazacyclododec-1-yl]propyl]amino]-1-deoxy-D-glucitol ligand of formula

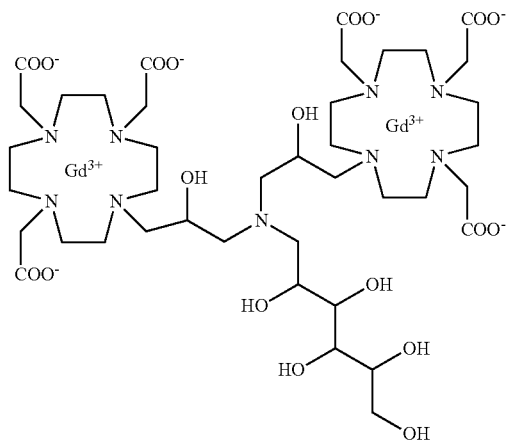

hereinafter otherwise identified as "dimeric complex compound 5" or, more simply as "Compound 5".

This complex compound shows interesting properties, especially in terms of relaxivity and tolerability that makes it suitable for use in the in vivo diagnostic imaging carried out with doses of the paramagnetic complex lower than those required by the contrast agents of the market.

A preparation process is moreover disclosed in the above international application, schematized in the following general Scheme 1:

Scheme 1

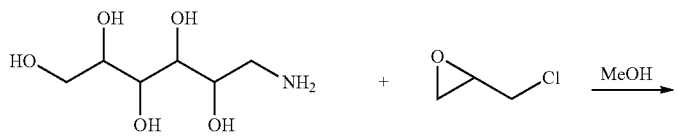

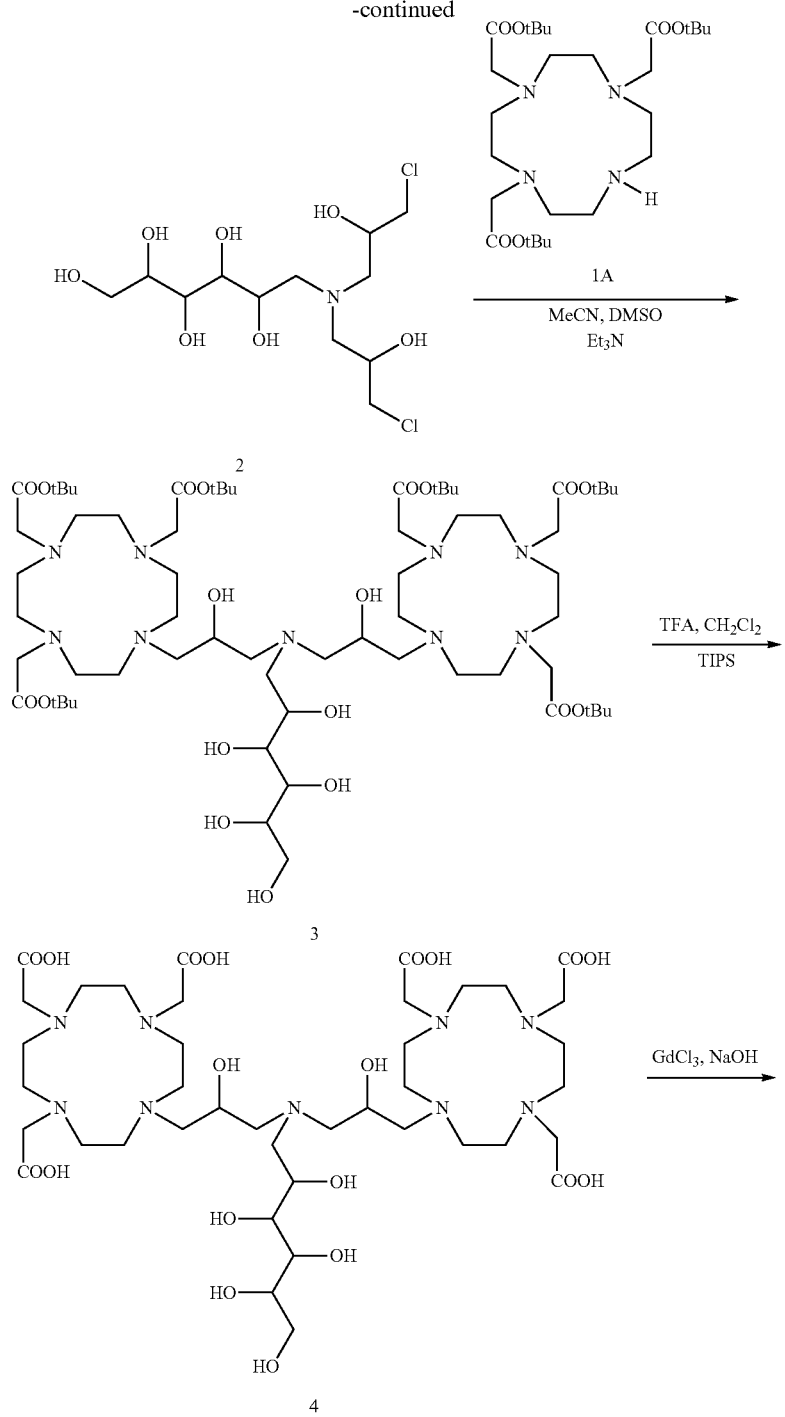

Main steps of the disclosed synthetic process comprise:
a) preparation and isolation of DO3A tri-tert-butyl ester (compound 1A) carried out substantially as disclosed in Org. Synth. 2008, 85, 10;
b) preparation of the intermediate 2 by alkylation of D-glucamine with epichlorohydrin (molar ratio 1:4.95) in MeOH at 50° C. for 26 h, and the isolation of the condensation product by evaporation of the crude reaction;
c) alkylation of DO3A tri-tert-butyl ester with the intermediate 2 in DMSO and Et$_3$N, evaporation and purification of the crude residue on Amberlite XAD® 1600 leading to give the protected ligand 3;
d) deprotection of the ligand 3 with TFA acid and TIPS in dichloromethane, evaporation of the crude reaction and purification of the residue on Amberlite XE 750;
e) complexation of the ligand 4 in water with stoichiometric addition of gadolinium chloride hexahydrate, and purification on Amberchrome CG161M resin of the crude product obtained by filtration and evaporation of the solution.

The process of requires the synthesis and isolation of each of the individual intermediates, which is generally carried out by evaporation to residue of the solvent. Such isolation steps, besides being unsuitable for a large-scale production, unavoidably result in a reduction in the overall yield and efficiency of the process. Moreover, the prior art process is not particularly suitable for working on larger scales, for example on industrial processes, because it encompasses the use of harsh materials that are difficult to handle, such TFA, TIPS and DCM, which might i.a. cause corrosion and thus wear out the synthesis apparatuses and/or might not be safe for the health of the workers.

Finally, the complexation step disclosed in WO 2017/098044 is not easily reproducible, i.a. because it depends on the precise weighing of the reactants of the complexation step and on the precise determination of the titles thereof. At least for this reason, the robustness of the process disclosed in WO 2017/098044 could be improved.

Accordingly, there is the need of a process for the preparation of the Gd(III) complexes disclosed in WO 2017/098044 that overcomes the above mentioned problems, in particular a process that is reproducible, robust, and that it is advantageous for large-scale production of the dimeric paramagnetic complexes disclosed in WO 2017/098044.

SUMMARY OF THE INVENTION

The present invention generally relates to an optimized process for the manufacturing of the dimeric complex compound 5 which includes preparation steps carried out one-pot and without isolation of the resulting intermediates which allow for both time saving and an improved overall yield and efficiency, as well as providing a final product containing low amounts of the toxic free gadolinium metal ions.

More particularly, the invention relates to a process for the manufacturing of the dimeric complex compound 5

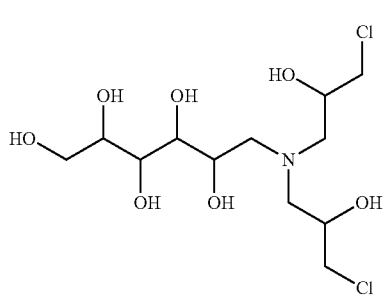

which comprises, as main steps:

1) preparing a solution of DO3A tri-tert-butyl ester of formula 1A

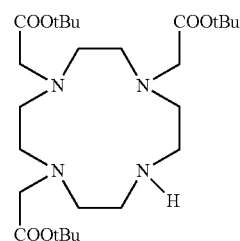

for example in an organic solvent;

2) preparing a solution of the intermediate of formula 2

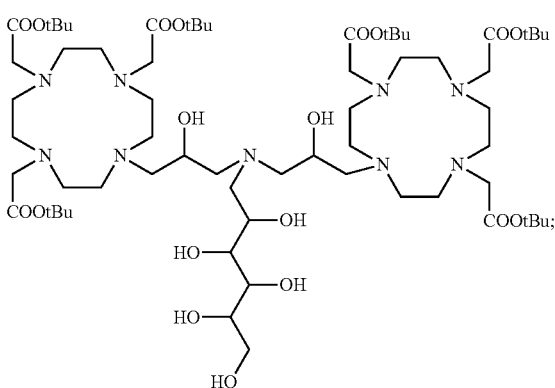

for example in an organic solvent;

3) admixing the solutions prepared according to steps 1) and 2) to obtain a solution of the protected ligand of formula 3

4) without isolating the protected ligand from the solution of step 3) removing the tert-butyl protecting groups from the protected ligand to obtain a solution of a respective free ligand of formula 4

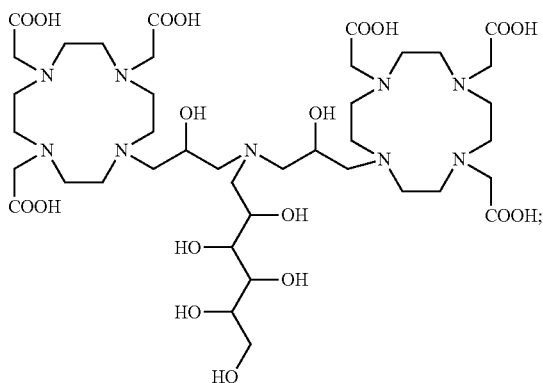

5) without isolating the free ligand of formula 4 from the obtained solution, adding a molar excess of gadolinium metal ions to the solution of step 4) to obtain a solution of the respective dimeric complex of formula 5;

6) adding to the solution of the respective dimeric complex of formula 5 a precipitating agent to precipitate a portion of free gadolinium metal ions as insoluble gadolinium salt; and 7) isolating of the dimeric complex.

Interestingly the process set out in claim 1 avoids or strongly reduces the use of harsh reagents, such as trifluoroacetic acid (TFA), and nasty solvents, such as dichloromethane, which are required in the process of the prior art and are difficult to handle when working on larger scales, for example on industrial processes.

Moreover, the process set out in claim 1 comprises steps that are carried out one-pot, which are suitable for a large-scale implementation, and which do not require the isolation of any of the prepared precursor (such as 1A) or intermediates. As a result, in addition to promote a reduction in process times, and of being easily implemented on larger scales as stated above, the process advantageously allows a significant increase in the overall process yield, from 10% (obtained with the process disclosed in WO2017098044) up to an overall yield of over 30%, such as of 33%.

Furthermore, the process of the invention is robust, thus being particularly suitable for large scale implementation. Indeed, the burden of the precise weighing of the reactants of the complexation step and of the determination of titles is heavily reduced due to the addition of a molar excess of gadolinium metal ions in step 5), which was not disclosed in the prior art process.

Moreover, step 6) provides for removing free gadolinium metal ions via precipitation. This purification step is less burdensome than removing the same by purification through columns (as carried out in the prior art document mentioned above). Adding a molar excess of gadolinium metal ions provides a higher amount of free gadolinium metal ions after complexation compared to the addition of a stoichiometric quantity, or less of a stoichiometric quantity, of gadolinium metal ions; however, it has been found that this higher amount of free gadolinium metal ions can be effectively and efficiently removed by carrying out the precipitation step 6) of the invention, i.e. by precipitating free gadolinium metal ions with a precipitating agent as herein disclosed. Accordingly, combining step 5) and step 6) provides a particularly effective removal of free gadolinium metal ions from the solution of the dimeric complex of formula 5 via a process that is robust and suitable for large-scale production.

As the process of the invention is robust, reproducible and efficient (at least yield-wise), it can be easily implemented for large-scale production of the dimeric complex 5.

The step 1) of the process generally comprises the preparation of a solution of DO3A tri-tert-butyl ester 1A. In one embodiment the solution is prepared in an organic solvent, e.g. by solubilizing in the solvent a commercial DO3A tri-tert-butyl ester, or a DO3A tri-tert-butyl ester prepared by using a known synthetic procedure.

In a preferred embodiment the solution of 1A is prepared just before its use, by converting a salt of the DO3A tri-tert-butyl ester, such as a hydrobromide salt to the respective free base 1A. The conversion, typically comprising the neutralization of the hydrobromide, is preferably carried out in an organic solvent and in the presence of a base or a basic salt (a salt that is the product of the neutralization of a strong base and a weak acid, which hydrolyzes by forming a basic solution). Then, the removal of formed salts and optional concentration of the filtered solution allows to achieve a solution of the DO3A tri-tert-butyl ester 1A in the organic solvent that is suitable for use as such in the subsequent step of the process, without requiring any purification or isolation of the ester.

Suitable organic solvents preferably include MeCN, propylene carbonate, ethanol, t-butanol, hexane, and the like. More preferably, the organic solvent is MeCN.

Suitable bases or basic salts for the neutralization of the starting hydrobromide for instance include strong bases and anion exchange resins such as, for example, Diaion PA308, Amberlite IRA 400, KOH, tBuOK, $Na_2CO_3$ and $K_2CO_3$, where the latter two are preferred. More preferably, the neutralization of the DO3A tri-tert-butyl ester hydrobromide is carried out in the presence of $K_2CO_3$.

The step 2) of the process comprises the preparation of the compound of formula 2, which may be obtained by alkylation of D-glucamine with epichlorohydrin. The alkylation is carried out in organic solvent, such as a dipolar organic solvent or in an aqueous mixture thereof. Suitable organic solvents for instance include DMAC, DMF, alcohols such as MeOH, and their mixtures. More preferably, the organic solvent is DMAC. The distillation of any aqueous solvent and/or epichlorohydrin excess from the mixture leads then to achieve a solution of the compound of formula 2 in the organic solvent which is suitable for use as such in the next step of the process, without isolation and/or further purification of the alkylation product.

The step 3) of the process essentially comprises the condensation (or coupling, as herein used interchangeably) of the intermediate compound of formula 2 with the DO3A tri-tert-butyl ester 1A with formation of the protected ligand of formula 3. The condensation reaction is preferably carried out in the presence of a base, e.g. acting as an acceptor of the formed HCl. Suitable bases for instance include anion exchange resins such as Amberlite GC 400, NMM, tBuOK, $Et_3N$, and DIPEA, wherein $Et_3N$ and DIPEA are preferred and DIPEA is particularly preferred.

In one embodiment the condensation reaction is carried out by addition of the base and the organic solution of DO3A tri-tert-butyl ester 1A directly collected from step 1) to the solution of the compound 2 collected from step 2), to give an organic crude solution comprising the condensation product of formula 3 in an organic solvent mixture. Then, a purification of the organic crude leading to obtain the purified product in a water/organic solvent mixture, and the optional final distillation of any organic solvent allow to achieve the protected ligand of formula 3 in an aqueous solvent or an aqueous solvent mixture which can be used as such in the next step of the process, without isolation and/or further purification of the protected ligand itself.

The step 4) of the process substantially comprises the removal of the carboxyl protecting groups from the protected ligand of formula 3 to give an aqueous solution or an aqueous mixture of the respective free ligand of formula 4. The deprotection by hydrolysis of tert-butyl protecting groups can be carried out in both acidic and basic conditions, by using reactants and conditions known to those skilled in the relevant art. In one embodiment, the deprotection is carried out by acidification of the aqueous solution or aqueous mixture of the protected ligand directly collected from step 3) of the process, to achieve an acidic solution of the free ligand of formula 4. The acidification is preferably carried out by addition of an acid, for instance selected from HCl, $H_2SO_4$, and $H_3PO_4$. Inorganic acid comprising a counterion having a single negative charge, such as HCl, HBr and the likes, are particularly preferred. In a preferred embodiment the deprotection is performed by using HCl. In a particularly preferred embodiment, the deprotection is carried out by heating and/or maintaining the temperature of the acidic reaction mixture to a temperature higher than 40° C., preferably higher than 40° C. and up to 60° C., more preferably within the range from 45 to 55° C. Then, the neutralization of the acidic solution, subsequent purification and partial concentration of the resulting mixture lead to collect an aqueous solution or aqueous mixture of the ligand 4, that is used as such in the complexation step, without isolation.

The step 5) comprises the complexation of the ligand with a molar excess of gadolinium metal ions, to the desired dimeric complex 5. The complexation reaction can conveniently be carried out by addition of a suitable Gd(III) derivative, particularly an oxide such as $Gd_2O_3$ or of a soluble gadolinium salt to the solution of the ligand. In one embodiment the complexation reaction is carried out by addition of the soluble gadolinium salt $GdCl_3$ to the solution of the ligand directly collected from step 4) of the process.

The step 6) comprises precipitating the free gadolinium metal ions that are present within the solution of the dimeric complex of formula 5. These free ions are present because they have been added in a molar excess in the previous step, and possibly because not all of the gadolinium added in the previous step has reacted with the ligand 4 to form the desired dimeric complex 5. The precipitation step 6) is carried out by adding a precipitating agent to precipitate a portion of free gadolinium metal ions as insoluble gadolinium salt. Preferred precipitation agents are selected from the group consisting of phosphate ($PO_4^{3-}$), monohydrogen phosphate ($HPO_4^{2-}$), dihydrogen phosphate ($H_2PO_4^{-}$), orthophosphoric acid ($H_3PO_4$), oxalate ($C_2O_4^{2-}$), hydrogen oxalate ($HC_2O_4^{-}$), and oxalic acid ($H_2C_2O_4$). In a preferred aspect, the precipitating agent is added in an amount of at least of 1.1 moles, preferably in an amount from 1.1 to 5 moles with respect to 1 mole of the amount of the dimeric complex 5. In a further preferred aspect, during and/or after the addition of the precipitating agent according to step 6), the pH is adjusted to and/or maintained higher than 4.5, preferably higher than 4.7, and possibly lower than 10.0, preferably lower than 9.0. In a further preferred aspect, after precipitation of the insoluble gadolinium salt, there is provided a step of removing e.g. filtering the obtained solution to remove the insoluble gadolinium salt from the solution, whereby the insoluble gadolinium salt is separated from such solution.

The resulting filtered mixture can be then further purified (through further purification steps) and concentrated to achieve solution of the desired dimeric complex 5 having the desired purity.

The step 7) comprises the final isolation of desired gadolinium complex 5. This step can conveniently be carried out according to know procedures. In one embodiment the solution of the purified complex collected from step 5) is spray-dried to give the desired product as a white solid satisfying the required purity specifications.

DETAILED DESCRIPTION OF THE INVENTION

In the present description, and unless otherwise provided, the term "intermediate" (e.g. used with reference to the compound of formula 2 deriving from the alkylation reaction of the D-glucamine with epichlorohydrin, or the protected ligand of formula 3) comprises within its meaning a molecule produced in the course of a chemical synthesis or preparation step of the process which is not itself the final product, but requires one (or more) further reactions e.g. alkylation/deprotection/complexation reaction(s) to give the final product of the process, namely the dimeric complex compound 5.

Unless otherwise provided, the term "precursor" (e.g. used with reference to the compound 1A) comprises within the meaning a molecule that participates in a chemical reaction promoting its transformation into another molecule, which includes or is derived from said precursor.

In the present description, the term "aqueous solvent" comprises within the meaning water, aqueous saline solutions, possibly including small amounts of organic solvents miscible with water, such as a volume percentage of 10% or lower of organic solvents miscible with water, preferably 8% or lower, and more preferably 5% or lower, for example because the process of the invention is carried out without isolating most of the intermediate products, thereby small amounts of organic solvents can be carried on through the upstream and first steps of the process. Preferably the aqueous solvent is water.

The expression "water/organic solvent mixture" or, more simply, "aqueous solvent mixture" as used herein interchangeably, comprises within the meaning a mixture of two or more solvents which comprises an aqueous solvent, such as a mixture of water and one or more organic solvents all miscible with each other, to give a homogeneous solvent mixture, wherein the volume percentage of the one or more organic solvents is higher than 10%, preferably higher than 15%, and more preferably higher than 20%. Suitable examples include mixtures of water and acetonitrile (or water/MeCN) used as eluents in the chromatographic purifications e.g. of the compound of formula 3, or the mixture of water/MeCN/DMAC e.g. resulting after dilution with water of the crude mixture resulting from the condensation reaction of step 3). According to a preferred aspect of the present invention, the one or more organic solvents within the aqueous solvent mixture (as well as within the aqueous solvent, when present) is not a harsh solvent or material; indeed, the aqueous solvent mixture preferably does not comprise harsh solvents such as TFA, TIPS and/or DCM.

Likewise, the expressions "aqueous solution" and "aqueous mixture" include in their meaning, respectively, a solution or a mixture containing water. Suitable examples include, respectively, a solution of one or more compounds, e.g. a reagent, an acid, a base or a reaction product in water (more in general, in an aqueous mixture) or in an aqueous solvent mixture, and a mixture, such as the water/organic mixture resulting from the addition of water or an aqueous solution to a reaction mixture in an organic solvent or solvent mixture.

In the present description the term "protecting group" (e.g. used with reference to the compound of formula 3) designates a protective group adapted for preserving the function of the group to which it is bound. Specifically, protective groups are used to preserve carboxyl functions. More specifically the term designates tert-butyl groups preserving the chelating function of carboxyl groups of the ligand by formation of tert-butyl esters [see, for a general reference on protecting groups and deprotecting conditions, T. W. Green and P. G. M. Wuts; *Protective Groups in Organic Synthesis*, Wiley, N.Y. 1999, third edition].

As used herein, and unless otherwise provided, the term "precipitating agent" refers to the agent added in step 6) that is, or that generates, an anion at least in the conditions of step 6) when added to the solution of dimeric complex 5 according to the process of the invention. Such anion is able to generate, through ionic bond(s) with the free gadolinium metal ions, an insoluble gadolinium salt as herein defined.

As used herein, and unless otherwise provided, the term "insoluble gadolinium salt" refers to the salt generated after addition of the precipitating agent as herein defined. The insoluble gadolinium salt comprises as a cation $Gd^{3+}$, and as a counter-anion the anion which is, or is generated by, the precipitating agent. At least in the conditions of step 6) of the process of the invention, and preferably also in the conditions of the steps downstream of step 6) at least until the filtration step, the insoluble gadolinium salt is present within the reaction mixture in a solid and filterable physical form; in these conditions, the mass parts of solvent required to dissolve 1 mass part of gadolinium salt is preferably 100 or higher, more preferably 1,000 or higher, and even more preferably 10,000 or higher. Examples of insoluble gadolinium salt are gadolinium phosphate and gadolinium oxalate. The term "soluble gadolinium salt" refers instead to the soluble gadolinium salt added during step 5) (typically $GdCl_3$) to carry out the complexation of the dimeric ligand 4, thereby obtaining the complex 5.

As used herein, and unless otherwise provided, the term "free gadolinium metal ions" refers to gadolinium ions, such as $[Gd(H_2O)_8]^{3+}$, that are present within a solution and that are not chelated by the dimeric ligands.

An embodiment of the invention relates to a process for the manufacturing of the dimeric compound 5 essentially as schematized in the following general synthetic Scheme 2

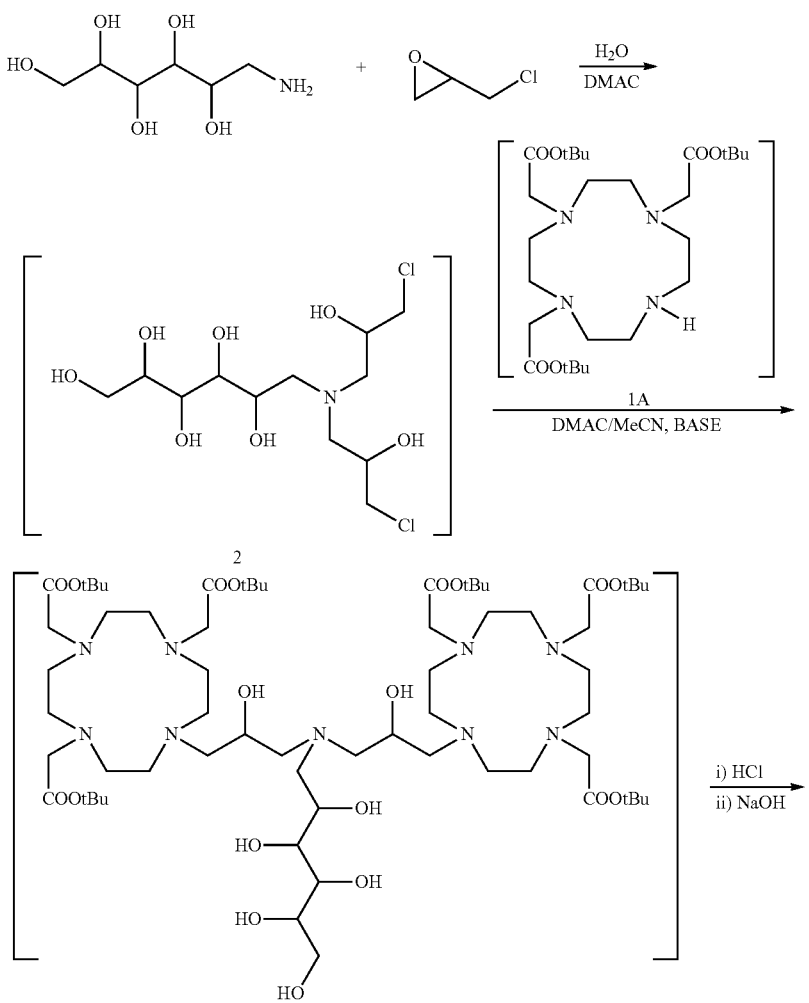

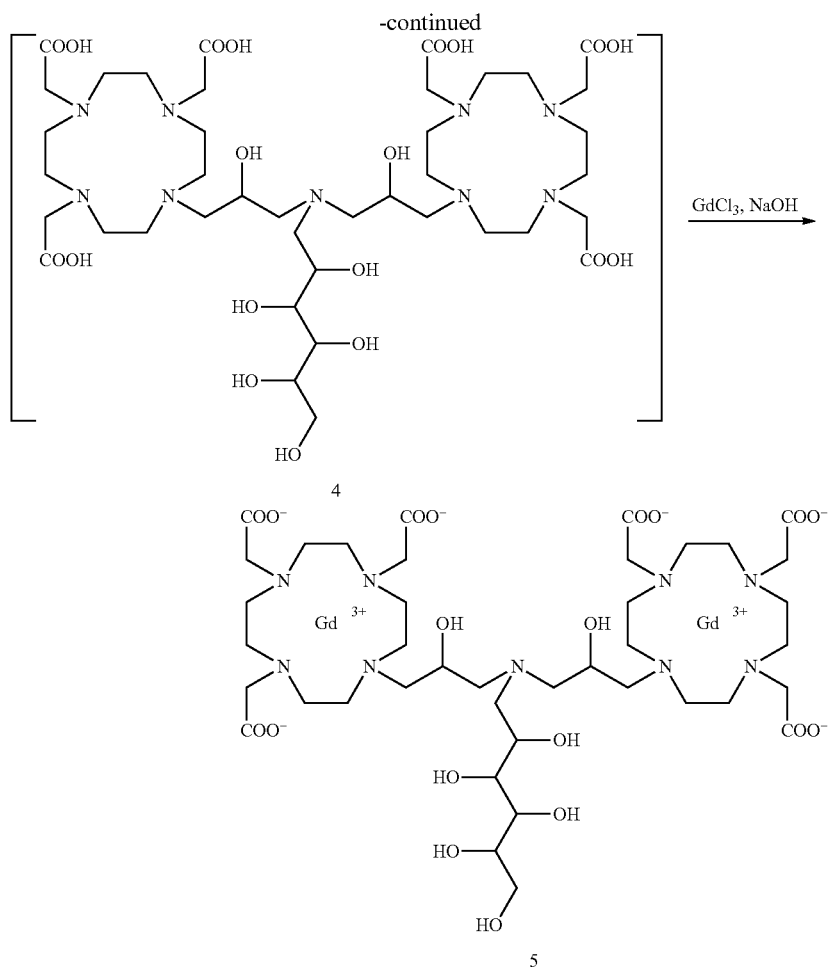

which comprises, as main steps:
1) neutralizing a hydrobromide salt of the DO3A tri-tert-butyl ester in an organic solvent, to give a solution of DO3A tri-tert-butyl ester 1A in the organic solvent;
2) reacting D-glucamine with epichlorohydrin to obtain a solution of the compound of formula 2 in an organic solvent such as DMAC; and, without isolation of the product
3) reacting the compound of formula 2 from step 2) with DO3A tri-tert-butyl ester 1A from step 1) in the presence of a base and optional concentration of the solution to give an organic crude, dilution of the organic crude with water, a water/organic solvent mixture and/or an optional aqueous solution to obtain a water/organic crude, purification of the water/organic crude and optional removal of any organic solvent to give an aqueous solution or an aqueous mixture of the protected ligand of formula 3; and, without isolation of the product
4) acidifying the solution of the protected ligand of formula 3 from step 3) while heating and/or maintaining the temperature of the reaction mixture to a temperature higher than 40° C. to give an acidic aqueous solution or aqueous mixture of the respective deprotected ligand 4, neutralizing the acidic solution and purifying the resulting neutral solution to give an aqueous solution or aqueous mixture of the deprotected ligand 4, and, without isolation of the latter,
5) adding a molar excess of gadolinium metal ions to the solution of the ligand 4 to obtain a solution of the corresponding complex compound 5;
6) adding to the solution of the corresponding complex compound 5 a precipitating agent to precipitate a portion of free gadolinium metal ions as insoluble gadolinium salt, whereby a solution of the corresponding complex compound 5 is obtained; and
7) isolating the complex.

Step 1

The first step of the process comprises preparing a solution of the DO3A tri-tert-butyl ester 1A in an organic solvent, such as MeCN, by converting a hydrobromide salt of the DO3A tri-tert-butyl ester to the respective free base directly in the organic solvent, in the presence of a base or a basic salt.

In a preferred embodiment the step 1) of the process comprises:
i) suspending a hydrobromide salt of the DO3A tri-tert-butyl ester together with a base or a basic salt such as $K_2CO_3$ in an organic solvent such as MeCN to obtain a suspension comprising formed salts;
ii) filtering the suspension; and
iii) collecting and optionally concentrating the filtered suspension, to obtain a solution of the DO3A tri-tert-butyl ester 1A in the organic solvent which is suitable for use as such in the subsequent condensation reaction, without requiring any purification or isolation of ester.

The ester hydrobromide and $K_2CO_3$ are preferably suspended in the organic solvent at room temperature to give a mixture that is then maintained under stirring at a temperature of from 20 to 30° C., preferably of about 25° C. for a time of from 16 to 30 h, preferably for 18-20 h. The mixture is then treated to remove the formed salts, preferably by filtration.

In a preferred embodiment, the solution resulting by filtration is subjected to a thermal concentration, for example by partial distillation of the solvent, to give a solution of the tri-tert-butyl ester 1A in MeCN with a final concentration of from 55 to 65% and preferably of about 60% (w/w) which is suitable for use as such in the subsequent condensation step of the process.

Step 2

The step comprises preparing a solution of the intermediate compound of formula 2 by reacting D-glucamine with epichlorohydrin. In one embodiment the reaction is carried out in a mixture of solvents, preferably in water/DMAC, by using a slight excess of epichlorohydrin over the stoichiometric amount, for example of from 2 to 3 and more preferably of about 2.2 moles of epichlorohydrin per mole of D-glucamine. Preferably, such reaction of step 2) is carried by using a slight excess of epichlorohydrin over the stoichiometric amount, for example from 2 to 3 moles, more preferably from 2.05 to 2.5 moles, and even more preferably about 2.2 moles of epichlorohydrin per mole of D-glucamine.

In a preferred embodiment the step 2) of the process comprises:
  i) adding an aqueous solution of D-glucamine to a solution of epichlorohydrin in DMAC to give the intermediate compound of formula 2 in a water/DMAC solvent mixture; and
  ii) removing the water from the solvent mixture, to obtain a solution of the compound of formula 2 in the organic solvent.

The addition of D-glucamine to the solution of epichlorohydrin is preferably carried out at room temperature, in a time of about 2 h, to give a mixture that is kept under stirring at a temperature of from 15 to 30° C., preferably from 15 to 25° C. and more preferably from 20 to 25° C., for a time of from 16 to 24 h, preferably from 16 to 20 h and more preferably of about 17 h.

The mixture is then distilled, to remove water and any optional epichlorohydrin residue. The distillation is preferably carried out at reduced pressure, and a temperature preferably of 40-65° C., leading to achieve a solution of the desired intermediate compound of formula 2 in DMAC with a residual water content preferably <2% w/w. The achieved solution is then used as such in the subsequent condensation reaction, without requiring any isolation or purification of the product.

Step 3

This step essentially comprises the condensation of the DO3A tri-tert-butyl ester 1A with the intermediate 2, in the presence of a base such as $Et_3N$ or, more preferably, DIPEA. The condensation is preferably carried out by admixing the base and the solutions of the ester 1A in MeCN from step 1) with the solution of the intermediate 2 in DMAC directly collected from step 2) to give a raw solution (or crude) comprising the protected ligand of formula 3 in the mixture of the MeCN/DMAC organic solvents that is then purified.

In one embodiment, the organic crude solution resulting from the condensation reaction is diluted with water or is partially concentrated and then diluted with water or an aqueous solvent mixture, preferably water/MeCN, to obtain a water/organic crude, or aqueous crude, as herein used interchangeably.

In a preferred embodiment, the water/organic crude thus obtained or, preferably, the organic crude resulting from the condensation reaction are added with an aqueous solution which promotes the precipitation of reaction salts, including DO3A tri-tert-butyl ester hydrochloride, which are then removed by filtration, to provide a water/organic filtered solution. The water/organic crude or the water/organic filtered solution are then purified, preferably by chromatography.

In one embodiment, the aqueous solution used to promote the precipitation of the hydrochloride salts is aqueous ammonia.

More particularly, the step 3) of the process preferably comprises:
  i) condensation of the intermediate compound of formula 2 from step 2) with DO3A tri-tert-butyl ester 1A from step 1) in the presence of a base, preferably DIPEA, to give an organic crude solution comprising the condensation product of formula 3 and reaction salts in the organic solvent mixture, and optional concentration of the organic crude;
  ii) dilution of the organic crude of step i) with water or a water/organic solvent mixture, preferably water/MeCN, to give a water/organic crude;
  iii) optional addition to the water/organic crude of an aqueous solution promoting the precipitation of reaction salts that are removed by filtration to give a water/organic filtered solution; or
  iv) dilution of the organic crude of step i) with the aqueous solution promoting the precipitation of reaction salts that are removed by filtration, to give a water/organic filtered solution;
  v) purification of the water/organic crude of step ii), or of the water/organic filtered solution of steps iii) or iv) to give a solution of the protected ligand of formula 3 in a water/organic solvent mixture that can be used in the next deprotection step of the process without requiring any isolation or further purification of the protected product; and
  vi) optional removal of any organic solvent from the mixture, to obtain a solution of the protected ligand of formula 3 in water, or more in general in an aqueous solvent, that is used in the next deprotection step of the process without requiring any isolation or further purification of the protected product.

The condensation reaction is preferably carried out by addition of the base and a solution of the ester 1A in MeCN collected from step 1) of the process to the solution of the intermediate compound of formula 2 in DMAC collected from step 2).

Suitable amounts of base and ester 1A are conveniently determined with respect to the amount of D-glucamine subjected to the reaction. In one embodiment, the condensation reaction is carried out by using from 1.6 to 2.4 moles and preferably about 1.8 moles of ester 1A, and from 2 to 4 moles, preferably about 2.3 moles of DIPEA per mole of starting D-glucamine subjected to reaction.

The addition is preferably performed at a temperature of 40-50° C. The condensation reaction is then carried out at a temperature of from 50 to 80° C., preferably from 65 to 75° C. for a time e.g. of 60-80 h, preferably of 70-75 h, to give a raw solution comprising the desired condensation product of formula 3 and hydrochloride salts in a MeCN/DMAC solvent mixture.

In one embodiment, the raw solution is then diluted with water to give a water/organic crude having, preferably, a concentration of about 25-30%, more preferably of about 25% (w/w). In one preferred embodiment, the aqueous crude comprises an amount of water which by weight is at least equal to the amount of the organic solvent, specifically MeCN in the mixture; more preferably the crude has a water:MeCN ratio of about 60:40.

The water/organic crude is then purified, preferably by chromatography, more preferably on resins, even more preferably on adsorbent resins, such as Amberlite XAD® 1600. In a preferred embodiment, the aqueous crude is purified on an adsorbent resin, such as Amberlite XAD® 1600, by using a water/MeCN mixture as eluent, allowing to achieve both the unreacted DO3A tri-tert-butyl ester 1A and the pure condensation product as separated fractions in a water/MeCN solvent mixture.

In another embodiment the raw solution resulting from the condensation reaction is first concentrated by removing at least a part of the MeCN, e.g. by distillation. The concentrated solution is then diluted with water or with a mixture of water:MeCN allowing to obtain a water/organic crude having the above water:MeCN ratio, that is then purified by chromatography, as above said.

Optionally, the water/organic crude obtained as above said is added with an aqueous solution such as aqueous ammonia which promotes, by cooling of the mixture, the precipitation of the unreacted DO3A tri-tert-butyl ester as hydrochloride, that is then removed by filtration and, optionally recycled. The filtered solution devoid of most of the chloride salts is then purified by chromatography on an adsorbent resin, such as Amberlite XAD® 1600 resin as above said, to give the residual DO3A tri-tert-butyl ester 1A and the pure condensation product as separated fractions in a water/organic, such as a water/MeCN, solvent mixture.

In a preferred embodiment, the aqueous solution, e.g. including aqueous ammonia is added directly into the organic raw solution resulting from the condensation reaction promoting, by cooling of the mixture, the precipitation of the unreacted DO3A tri-tert-butyl ester as hydrochloride that is then removed by filtration and, optionally recycled. The filtrate devoid of most of the chloride salts is then purified by chromatography on an adsorbent resin, such as Amberlite XAD® 1600 resin as above said, to give the residual DO3A tri-tert-butyl ester 1A and the pure condensation product as separated fractions in a water/organic, such as a water/MeCN, solvent mixture.

The optional final distillation of the organic solvent, e.g. under reduced pressure, from pure fractions leads then to achieve the condensation product of formula 3 in an aqueous solution with a final concentration of 5-15% (w/w), preferably of about 10% (w/w), that is suitable for use in the subsequent deprotection step as such, without requiring any isolation or additional purification of the intermediate.

Interestingly, the above procedural steps allow to obtain the protected condensation product 3 in an aqueous solvent or aqueous solvent mixtures, thus making it possible to carry out its deprotection and complexation to the final complex 5 by using water, and more in general aqueous solvents or aqueous solvent mixtures, as the only or one of the main reaction solvents. The protected condensation product 3 in an aqueous solvent can be obtained according to various methods known to the skilled person. For example, as stated above, the organic crude solution of compound of formula 3, e.g. obtained by reacting the compound of formula 2 from step 2) with DO3A tri-tert-butyl ester 1A from step 1), can be diluted with water, a water/organic solvent mixture, or an aqueous solution, thus obtaining a water/organic crude. Before removal of the organic solvent, the water/organic crude can be purified via chromatography, preferably via a resin, and more preferably via an adsorbent resin, such as Amberlite XAD® 1600. Then, the organic solvent can be removed to obtain the aqueous solution of the compound of formula 3, for example by distillation e.g. under reduced pressure. Also the protected condensation product 3 in an aqueous solvent mixture can be achieved according to various methods known to the skilled person. For example, the organic crude solution of compound of formula 3, e.g. obtained by reacting the compound of formula 2 from step 2) with DO3A tri-tert-butyl ester 1A from step 1), can be diluted with water, a water/organic solvent mixture, or an aqueous solution, thus obtaining a water/organic solution to be used in the subsequent steps without isolation of the product 3.

Therefore, according to a preferred aspect of the present invention, step 3) may further comprise the further step of converting the solution of a compound of formula 3 to an aqueous solution of, or to an aqueous mixture of, a compound of formula 3. Preferably, this further step is carried out by: (i) diluting the solution of a compound of formula 3 with water, a water/organic solvent mixture, or an aqueous solution, thus obtaining an aqueous mixture (or a water/organic solution), and (ii) optionally removing the organic solvent, e.g. by distillation, thus obtaining an aqueous solution.

Step 4

This step comprises the deprotection of the protected ligand of formula 3 by removing carboxyl protecting groups leading to achieve an aqueous solution or aqueous mixture of the respective free ligand 4. The reaction is preferably carried out by acidification of the aqueous solution or mixture of protected ligand of formula 3 directly collected from step 3) of the process, and even more preferably by heating and/or maintaining the temperature of the reaction mixture to a temperature higher than 40° C. during and/or after the acidification of the solution.

In one embodiment the step 4) of the process comprises:
i) Addition of an acid to the aqueous solution or aqueous mixture of the compound of formula 3 collected from step 3), then and/or during such addition, heating and/or maintaining the temperature of the solution to a temperature higher than 40° C., preferably higher than 40° C. and up to 60° C., more preferably within the range from 45 to 55° C. to achieve acidic solution of the free ligand 4;
ii) Addition of a base to the acidic solution, to achieve a substantially neutralized solution of the ligand 4;
iii) Optionally, purification of the neutralized solution (e.g. via distillation) and subsequent optional concentration, to give an aqueous solution or aqueous mixture of the free ligand 4 that is suitable for use as such in the next complexation reaction, without requiring any isolation of the ligand.

In one embodiment the solution of the protected compound of formula 3 is acidified by addition of an acid, preferably of an inorganic acid, more preferably of an inorganic acid comprising a counterion having a single negative charge, such as 34% aqueous HCl. Inorganic acids comprising a counterion having a single negative charge are particularly preferred as these acids tend not to interact with free gadolinium metal ions, and as they can be more easily removed during optional purification processes downstream (e.g. nanofiltration).

This deprotection step 4) is very advantageous, in particular when carried out within the temperature ranges above, because it allows obtaining very short deprotection times, in particular reaction times below 24 hours, for example within the range of 8 to 20 hours, preferably of 12 to 18 hours, more preferably 16 hours.

Moreover, this deprotection step 4), in particular when carried out within the temperature ranges above, provides for deprotecting the protected dimeric ligand by using low amounts of acid. Indeed, the acidification is performed by using for example an amount from 10 to 45 moles, preferably from 10 to 35 moles, more preferably from 15 to 25 moles of acid, such as the ones above, and preferably of HCl, vs. 1 mol of the protected compound 3. This provides the advantage of saving reagents, as well as reducing the production of salts during the deprotection step. For example, when HCl is used for acidifying the solution, using a low amount of HCl will reduce the subsequent amount of NaCl salt that is formed when NaOH is used in to neutralize the deprotected dimeric ligand; similar examples can also be brought when other acids and bases are used in their respective steps.

As stated above, during and/or preferably after the addition of the acid, the temperature of the solution is preferably heated and/or maintained higher than 40° C., more preferably higher than 40° C. and up to 60° C., and even more preferably within the range from 45 to 55° C. The resulting solution is then maintained under stirring within the temperature ranges above for from a time below 24 hours, for example within the range from 8 to 20 hours, preferably from 12 to 18 hours, more preferably 16 hours, by following the deprotection of the ligand e.g. by chromatography.

The acidic solution is then cooled e.g. at 25° C., and then is neutralized by addition of a base, preferably NaOH, to achieve a raw solution with a final pH from 4 to 7, preferably from 5 to 6, more preferably from 5.3 to 5.7, even more preferably to 5.5. which can be then purified.

By carrying out the deprotection step 4) as herein disclosed, a solution comprising the correspondent deprotected dimeric ligand 4 and the alcohol t-butanol is obtained. Thus, according to a further preferred embodiment, preferably before the complexation step 5), tBuOH is removed from the solution comprising the deprotected dimeric ligand 4, preferably by distilling such solution. According to a preferred embodiment, the solution comprising the dimeric ligand 4 is distilled until the final concentration of dimeric ligand 4 is comprised in the range from 8% to 12% (w/w), more preferably from 9% to 11% (w/w), and even more preferably is 10% (w/w).

Advantageously, the above procedure comprises using water as the sole or one of the main reaction solvent, thus avoiding or reducing the use of organic solvents, and in particular of harsh solvents, such as DCM, and of harsh reactant, such as TFA and TIPS, which are required in the process of above-mentioned prior art. These harsh materials are difficult to handle, and are thus unsuitable for use in large-scale productions. Moreover, this step leads to achieve the desired ligand in an aqueous solution or aqueous mixture ready for use in the complexation reaction, without requiring its isolation.

Step 5

The step comprises the complexation of the dimeric ligand of formula 4 with gadolinium ions to achieve an aqueous solution or aqueous mixture of the desired chelated complex 5.

More particularly, the step preferably comprises addition of a molar excess of a soluble gadolinium salt, such as $GdCl_3$ to the solution of the ligand collected from step 4) to obtain a mixture comprising the dimeric chelated complex 5.

Since the deprotected dimeric ligand of formula 4 has two chelating moieties, and one dimeric ligand can thus chelate two gadolinium metal ions, the term "molar excess" when referring to step 5) of the process of the invention refers to an amount of moles of gadolinium metal ions that is more than twice than the amount of moles of the dimeric ligand of formula 4. Accordingly, the term "molar excess", when referring to step 5) of the process of the invention, refers to more than 2 moles of gadolinium metal ions with respect to 1 mole of dimeric ligand. For example, 2.05 moles or more, preferably from 2.05 to 2.50 moles, more preferably up to 2.20 moles, and even more preferably up to 2.12 moles of gadolinium metal ions are added to the solution of step 4) vs. 1 mole of deprotected dimeric ligand of formula 4.

The reaction is preferably carried out by addition of $GdCl_3$ directly to the solution of the ligand collected from the previous step of the process. The addition is preferably performed at a temperature within the range from 20 to 50° C., more preferably from 30 to 45° C., and even more preferably from 37 to 43° C. After adding the gadolinium ions according to step 5), the reaction mixture is preferably maintained, for example at the temperature ranges provided above, for a time from 1 to 5 hours, more preferably from 2 to 4 hours, before carrying out the subsequent step(s).

After the addition, the pH of the resulting mixture is adjusted to a value in the range from 5.0 to 7.0, more preferably from 5.0 to 6.0, for example for a time and/or at the temperature as provided above, for example by addition of a base, preferably NaOH.

As stated above, step 5) is particularly advantageous because the burden of the precise weighing of the reactants of the complexation step and of the determination of titles is heavily reduced due to the addition of a molar excess of gadolinium metal ions, thereby improving robustness of the overall process. As this process is particularly robust, reproducible and efficient, it can be even more easily implemented for large-scale production.

According to a preferred embodiment, after step 5), and optionally before step 6), the process of the invention comprises the further step of desalting the solution of the dimeric complex of formula 5, preferably via nanofiltration. This desalting (e.g. nanofiltration) step allows removing the salts produced in complexation step, e.g. the salts generated after addition of the soluble gadolinium salt, as well as the salts generated in the deprotection step 4). The desalting step does not remove free gadolinium metal ions nor monogadolinated complexes, and is useful to remove salts in order to improve the subsequent optional steps for removing the precipitating agent.

The desalting step can be carried out until the value of conductivity of the solution is 5.0 mS/cm or lower, preferably 1 mS/cm or lower, and even more preferably 0.8 mS/cm or lower.

Step 6

Step 6) of the process of the invention provides for adding to the solution of the previous step a precipitating agent to precipitate a portion of the free gadolinium metal ions that are present within such solution. Indeed, this step allows precipitating a portion of free gadolinium metal ions, and in particular a substantial portion thereof: as showed in the Experimental section below, the precipitation step 6) allows precipitating a substantial portion of free gadolinium metal ions that is present after the complexation step 5), whereby the content of free gadolinium metal ions is reduced from almost tens of thousands ppm to just above a hundred ppm or even tens ppm (vs. the amount of dimeric complex 5). In particular, this step provides for manufacturing a solution comprising the dimeric complex 5 containing an amount of free gadolinium metal ions of less than 350 ppm, preferably less than 150 ppm, more preferably less than 100 ppm, and even more preferably less than 80 ppm, vs. the amount of gadolinium complex 5. According to the present invention, high ppm values of free gadolinium metal ions, e.g. the ppm values before the precipitation step, or after addition of potassium hydrogen tartrate for Example 8, or in general ppm values of 4000 ppm or higher, are determined by conventional complexometric titration with EDTA in the presence of xylenol orange, while low ppm values of free gadolinium metal ions, e.g. the ppm values after the precipitation step, or in general ppm values lower than 4000 ppm, are determined by carrying out the Procedure 5 as set out in the Experimental section below.

In order to obtain a precipitation of free gadolinium metal ions and to avoid generation of mono-gadolinated complexes, the precipitating agent is preferably at least one selected from the group consisting of phosphate ($PO_4^{3-}$), monohydrogen phosphate ($HPO_4^{2-}$), dihydrogen phosphate ($H_2PO_4^-$), orthophosphoric acid ($H_3PO_4$), oxalate ($C_2O_4^{2-}$), hydrogen oxalate ($HC_2O_4^-$), and oxalic acid ($H_2C_2O_4$). Preferably, the precipitating agent is at least one anion selected from the group consisting of phosphate ($PO_4^{3-}$), oxalate ($C_2O_4^{2-}$), and monohydrogen phosphate ($HPO_4^{2-}$), and more preferably is monohydrogen phosphate ($HPO_4^{2-}$).

Mono-gadolinated complexes are Gd(III) complexes wherein the dimeric ligand 5 chelates only one gadolinium ion instead of two. These mono-gadolinated complexes do not show the favourable relaxometric properties of the di-gadolinated Gd(III) complexes 5. It is cumbersome and difficult to efficiently remove these mono-gadolinated complexes from the solution obtained from the complexation step because mono-gadolinated complexes have very similar physical characteristics to di-gadolinated complexes. Accordingly, the preferred embodiments of step 6) provides for avoiding the generation of mono-gadolinated complexes during or after the complexation step as much as possible; this is particularly true compared to the process discloses in the prior art mentioned above, which provides solutions of the dimeric gadolinium complex comprising higher amounts of mono-gadolinated complexes.

According to a preferred embodiment of step 6), the precipitating agent is preferably added at least in stoichiometric amounts with respect to the free gadolinium metal ions within the solution of the dimeric complex of formula 5 obtained from step 5). Advantageously, the precipitating agent is added in an amount of at least of 1.1 moles, preferably in an amount from 1.1 to 5 moles, more preferably from 1.2 to 3 moles, even more preferably from 1.4 to 2.5 moles, and most preferably from 1.4 to 1.6 moles, with respect to 1 mole of gadolinium metal ions within the solution of the dimeric complex of formula 5 obtained from step 5). As demonstrated in the experimental section also by means of comparative examples, adding these preferred amounts of precipitating agent provides solutions containing both low amounts of free gadolinium metal ions, i.e. amounts lower than the ones specified above, and of mono-gadolinated complexes, i.e. amounts lower than 550 ppm, preferably lower than the LoQ of the method used to determine the amount of mono-gadolinated complexes (<400 ppm vs. the amount of gadolinium complex), after the optional filtration step and before the optional further purification steps. On the contrary, when the precipitating agent is added in step 6) in greater amounts with respect to the preferred amounts above, the resulting solution might contain a high amount of mono-gadolinated complex, i.e. an amount higher than 600 ppm. These ppm values of mono-gadolinated complex, as well as all ppm values of mono-gadolinated complex in the present invention, are determined by carrying out the Procedure 6 as set out in the Experimental section below.

When step 6) of the process of the invention is carried out by adding the preferred amounts of precipitating agent as specified above, the process of the invention may preferably comprise the further step of determining the amount of free gadolinium metal ions within the solution of the dimeric complex of formula 5 obtained from step 5) before adding the precipitating agent, whereby the precipitating agent can be added in the preferred amount as specified above. This determination step can be carried out according to known methods for determining the amount of free gadolinium metal ions, for example according to the method herein disclosed.

Step 6) is preferably carried out by maintaining the temperature of the solution within the range from 15 to 40° C., more preferably from 20 to 30° C. After adding the precipitating agent, the reaction mixture is preferably maintained, for example at the temperature ranges provided above, for a time from 1 to 4 hours, preferably from 1.5 to 3 hours, more preferably of 2 hours, before carrying out the optional subsequent step(s).

In a preferred embodiment, during and/or after the addition of the precipitating agent according to step 6), the pH is adjusted to and/or maintained at a value of 4.5 or higher, preferably of 4.7 or higher, more preferably of 4.9 or higher, even more preferably of 5.5 or higher, for example for a time and/or a temperature as provided in paragraph above. Preferably, this pH is maintained at least until the precipitated insoluble gadolinium salt is filtered out from the solution of the gadolinium complex. As demonstrated in the experimental section below also by means of comparative examples, applicant has surprisingly found that precipitating free gadolinium metal ions while adjusting and/or maintaining the pH at these values, a solution containing particularly low amounts of mono-gadolinated complexes after the optional filtration step and before the optional further purification steps is obtained, for example a solution containing an amount lower than 550 ppm, preferably and lower than 400 ppm of mono-gadolinated complexes vs. the gadolinium complex.

According to a further preferred embodiment, during and/or after the addition of the precipitating agent according to step 6), the pH can be adjusted to and/or maintained such that it is higher than the values indicated above, and that is 10.0 or lower, preferably 9.0 or lower, more preferably 8.5 or lower, even more preferably 7.5 or lower, and most preferably 6.5 or lower, for example for a time and/or a temperature as provided above. Preferably, this pH is maintained at least until the precipitated insoluble gadolinium salt is filtered out from the solution of the gadolinium complex. Applicant has surprisingly found that by operating below these pH values, the amount of free gadolinium metal ions within the solution after the precipitation step and before the optional further purification steps is particularly lowered.

According to a more preferred embodiment, during and/or after the addition of the precipitating agent according to step 6), the pH can be adjusted to and/or maintained in the range from 4.5 to 9.0, more preferably from 4.7 to 8.5, even more preferably from 4.9 to 7.3, and most preferably from 6 to 6.5 or from 5.5 to 6.5, for example for a time and/or a temperature as provided above. Preferably, this pH is maintained at least until the precipitated insoluble gadolinium salt is filtered out from the solution of the gadolinium complex. Applicant has surprisingly found that adjusting and/or maintaining the pH within the ranges indicated above allows obtaining solutions having a particular low content of free gadolinium metal ions and of mono-gadolinated complexes after the optional filtration step and before the optional further purification steps, for example a content lower compared to the same process wherein the pH is not adjusted and/or maintained at such pH.

The pH adjustment can be done for example by adding a suitable acid, e.g. HCl, or a suitable base, e.g. NaOH, to the solution. This adjustment is particularly useful to counteract the possible pH changes caused by the addition of the precipitating agent. It is evident that if the addition of the precipitating agent does not cause a change in pH such that the pH of the resulting solution falls outside the preferred ranges disclosed above (e.g. because the pKa of the precipitating agent is within the preferred values above and/or because the precipitating agent is added in low amounts whereby the pH of the resulting solution does not fall outside the preferred ranges disclosed above), then pH adjustment may not be necessary.

Preferably, the pH according to the preferred values disclosed above is maintained at least until the precipitated insoluble gadolinium salt is filtered out from the solution of the gadolinium complex.

In a further preferred embodiment, after step 6), and preferably before step 7), the process of the invention further comprises the step of filtering the obtained solution of gadolinium complex 5 after addition of the precipitating agent to remove the precipitated insoluble gadolinium salt from the solution, whereby the precipitated insoluble gadolinium salt is separated from such solution. This filtration step can be carried out according to any filtration method known in the art, for example by using pharmaceutical membrane filters.

In a further preferred embodiment, the process of the invention comprises the further step of treating the solution of gadolinium complex obtained after step 6) to remove, if present, the precipitating agent that have not reacted with the free gadolinium metal ions to form the insoluble gadolinium salt. This treatment step does not remove free gadolinium metal ions nor mono-gadolinated complexes.

This treatment step can be carried out for example by loading the solution of gadolinium complex on at least one ionic exchange resin, preferably at a flow rate from 1 to 3 BV/h. Alternatively, or together with loading the complex on at least one ionic exchange resin, the treatment step can be carried out by (A) adding to the solution of dimeric complex 5 a cation able to precipitate the anion that is, or is generated by, the precipitating agent, whereby at least part of such anion precipitates as a salt together with such cation, and (B) removing the salt thus formed by means of a filtration step, such as the one disclosed above. Advantageously, only one filtration step can be carried out to remove both the precipitated insoluble gadolinium salt and the salt formed by the precipitating agent and the precipitating cation.

In an embodiment, the present invention comprises at least one further purification step after step 6), and preferably after the treatment step for removal of the precipitating agent (if carried out). This further purification step is useful to further reduce the residual amount of free gadolinium metal ions that is present after the precipitation of step 6), in order to provide a solution of gadolinium complex with a content of free gadolinium metal ions as low as possible. In particular, according to this embodiment of the method of the invention, the larger portion of free gadolinium metal ions is removed by the precipitation step 6) (wherein the amount of free gadolinium metal ions is reduced from thousands of ppm to few hundreds, or even to tens of ppm, vs. gadolinium complex 5), and a smaller portion thereof is removed by the at least one further purification step.

The further purification step is preferably carried out by chromatography, preferably on resins, such as adsorbent resins.

In one embodiment the further purification step comprises the elution of the mixture resulting from the complexation reaction on a polymeric resin, preferably a Amberlite XAD® 1600 resins.

In another embodiment, the purification comprises a first elution of the mixture resulting from the complexation reaction on a chelating resin, for instance selected from Hi Trap IMAC FF, Lewatit MonoPlus TP 260, Lewatit TP 208, IRC748I, DIAION CR11, SiliaMets AMPA and SiliaMets DOTA, and preferably from Diaion CR11 and Amberlite IRC748, allowing to minimize any optional free gadolinium content, and the additional purification of the collected eluate on a polymeric resin, such as a Amberlite XAD® 1600 resin.

According to a practical implementation, a mixture adjusted to an about neutral pH value is properly purified by elution on Amberlite XAD® 1600 resin.

The mixtures resulting from regulation of the solution pH to lower values, such as 5-5.6, are otherwise preferably eluted first on a chelating resin such as the Amberlite IRC748 or the Diaion CR11 resin. The collected eluates are then preferably re-adjusted to a pH value of about 5.5-6 and concentrated, preferably under vacuum at 50° C. to obtain an aqueous solution or aqueous mixture of the dimeric complex with a concentration preferably of about 25% (w/w) that is then purified on Amberlite XAD® 1600 resin.

Collected fractions are then optionally treated with charcoal and filtered. The resulting filtered solution is then preferably concentrated, for instance by distillation under vacuum at 45-55° C. to give a solution of the dimeric complex 5 with a final concentration of about 25% (w/w). Step 7

The dimeric complex of formula 5 is then isolated. The complex can be isolated from the aqueous solution or aqueous mixture from step 6) for instance by lyophilization or by spray-drying. In one preferred embodiment the desired dimeric complex is obtained as a white solid by spray-drying the solution directly collected from step 6) of the process.

The overall yield of the process, determined from the limiting reactant as free base DO3A tri-tert-butyl ester 1A, is higher than 30%, such as 33%.

Interestingly the above process comprises steps that are carried out one-pot, which are suitable for a large-scale implementation, and which do not require the isolation of any of the prepared precursor (such as the compound of formula 1A) or reaction intermediates. As a result, the synthetic approach object of the present invention allows to achieve the final product with a >3-fold increase in the overall yield compared to the process disclosed in WO2017098044.

In addition, the lack of intermediates isolation allows for a reduction of the overall times process.

Moreover, the proposed process comprises the use of water, or more in general of aqueous solvent or aqueous solvent mixture, as the reaction solvent in all the steps following the preparation of the coupling product 3. In particular, when the compound of formula 3 is prepared in step 3) in an organic solvent, e.g. when it is prepared by reacting the compound of formula 2 from step 2) with DO3A tri-tert-butyl ester 1A from step 1), the organic solvent can be replaced with an aqueous one or with an aqueous mixture by methods known to the skilled person, e.g. by first diluting with water, a water/organic solvent mixture, or an aqueous solution the organic solution of the compound of formula 3, and then optionally by removing the organic solvent to obtain an aqueous solution of the compound of formula 3. Using aqueous solvents or aqueous solvent mixtures as reaction solvent in all steps following the preparation of the coupling is very advantageous, particularly from the standpoint of costs, environmental impact, and ease of implementation in industrial scale. Indeed, the process disclosed in WO2017098044, uses solvent such as DCM and materials such as TFA and TIPS that beside being expensive are also difficult to handle, particularly when scaling the process on an industrial scale, and might not be safe as well. As the process of the invention avoids or strongly reduces the use of organic solvents by using aqueous solvents or aqueous solvent mixtures in all the steps following the preparation of the compound of formula 3, the problem of the prior art process is solved by the present invention because the latter is suitable, and can be easily implemented, for working on larger scales, for example for working in industrial processes. Moreover, the process of the invention surprisingly provides very high yields of the isolated dimeric complex, in particular yields that are higher than the ones of the prior art process, even though it comprises only using aqueous solvents or aqueous solvent mixtures following the preparation of the compound of formula 3.

Moreover, the process of the invention overall is more robust, faster, safer, has higher yield, and provides a purer product compared to the process of the prior art WO 2017/098044.

In view of all the advantages stated above, it can be understood that the process of the invention can be easily implemented for large scale synthesis of the dimeric complex 5.

All solvents and starting materials, including reactants such as epichlorohydrin, D-glucamine, and the hydrobromide salt of DO3A tri-tert-butyl ester are commercially available, or can be obtained according to know procedures.

In a preferred embodiment, the hydrobromide salt of the DO3A tri-tert-butyl ester used as starting material for the preparation of a solution of the respective ester 1A is prepared by using the manufacturing process described in the co-pending EP19215900.2 patent application (same applicant as the present application) and exemplified below, in the experimental section of the description, and stored until the use.

Non-limiting examples of preferred embodiments of the process of the invention are reported in the following section, aimed to illustrate the invention in greater detail without limiting its scope.

EXPERIMENTAL PART

Abbreviations and Definition of Terms

DO3A tri-tert-butyl ester: tri-tert-butyl 1,4,7,10-tetraazacyclododecane-1,4,7-triacetate
DO3A tri-tert-butyl ester-HBr: tri-tert-butyl 1,4,7,10-tetraazacyclododecane-1,4,7-triacetate hydrobromide salt
TAZA: 1,4,7,10-tetraazacyclododecane
tBuOK Potassium tert-butoxide
DMAC N,N-dimethylacetamide
DMC Dichloromethane
DIPEA N,N-diisopropylethylamine
HCl Hydrocloric acid
MeCN Acetonitrile
NaOH Sodium hydroxyde
$NH_3$ Ammonia
MRI Magnetic Resonance Imaging
MeCN Acetonitrile
NMM N-methylmorpholine
$K_2CO_3$ Potassium carbonate
TFA Trifluorocetic acid
TIPS triisopropylsilane
FLD Fluorescence detector
UV/Vis Ultraviolet/Visible HPLC Characterization of the Obtained Compounds and Determination of Free Gadolinium Metal Ions (Free-Gd) or Mono-Gadolinated Complex (Mono-Gd).

Procedure 1: HPLC Characterization and Determination of the Assay of the DO3A-Tri-Tert-Butyl Ester Chromatographic Conditions

| | |
|---|---|
| HPLC system | Liquid chromatograph (e.g. Agilent 1100), equipped with solvent delivery system, autosampler, column thermostat, degasser and diode array detector or variable wavelength detector (or equivalent). |
| Stationary phase: | Zorbax Eclipse XDB-C8, 5 µm, 150 × 4.6 mm |
| Column temperature | 45° C. |
| Mobile phase: | A: 0.01M $K_2HPO_4$, 0.017M $H_3PO_4$ B: Acetonitrile |

| Elution: Gradient | Time (min) | % B |
|---|---|---|
| | 0 | 5 |
| | 30 | 80 |
| | 35 | 80 |
| | 38 | 5 |
| | 45 | 5 |

| | |
|---|---|
| Flow | 1 mL/min |
| Temperature | 45° C. |
| Detection | UV, 210 nm, Bw = 8 nm; Reference 360 nm, Bw = 100 nm |
| Injection volume | 10 µL |
| Stop time | 35 min |
| Reference peak | DO3A 3tBu |
| Retention time | DO3A 3tBu ≅ 14-15 min. |

Procedure 2: HPLC Method for Monitoring the Formation of Intermediate 2

This method is employed for monitoring the mixture at the end of the alkylation of the D-glucamine and after distillation of the water.

Chromatographic Conditions

| | |
|---|---|
| HPLC system: | Liquid chromatograph (e.g. Agilent 1100), equipped with solvent delivery system, autosampler, column thermostat, degasser and diode array detector or variable wavelength detector (or equivalent) |
| Stationary phase: | SeQuant ZIC-cHilic 3 µm, 150 × 2.1 mm (Merck P.N. 1.50658.0001) |
| Column Temperature: | 40° C. |
| Mobile phase: | gradient elution Eluent A = 5 mM ammonium acetate Eluent B = ACN/MeOH, 75/25 |

| Elution: Gradient | Time (min) | % B |
|---|---|---|
| | 0 | 97 |
| | 5 | 97 |
| | 30 | 20 |
| | 40 | 20 |

| | 45 | 97 |
| --- | --- | --- |
| | 60 | 97 |

| | |
| --- | --- |
| Flow rate: | 0.25 mL/min |
| Detection: | UV, 210-240 nm |
| Injection volume: | 10 µL |
| Run time: | 60 min |
| Dilution solution | ACN/MeOH, 75/25 |
| Sample preparation: | add 200 µL of 5 mM ammonium acetate solution to 75 µL of mixture and dilute to 5 mL with dilution solution. |

Sample preparation: add 200 µL of 5 mM ammonium acetate solution to 75 UL of mixture and dilute to 5 mL with dilution solution.

Procedure 3: HPLC Method for Monitoring the Formation and the Purification of Intermediate 3

General Procedure

The method is used for monitoring the formation of the Intermediate 3 and the purification step.

Analytical Conditions

| | |
| --- | --- |
| HPLC system | Liquid chromatograph Agilent 1100 |
| Stationary phase: | Gemini, 5 µm, 250 × 4.6 mm (Phenomenex, item 00G-4435-EO) |
| Column temperature | 40° C. |
| Mobile phase: | A: mobile phase A<br>B: MeCN |

| Elution: Gradient | Time (min) | % B |
| --- | --- | --- |
| | 0 | 40 |
| | 5 | 40 |
| | 30 | 90 |
| | 35 | 90 |
| | 36 | 40 |
| | 45 | 40 |

| | |
| --- | --- |
| Flow | 0.7 mL/min |
| Detection | UV/210 nm |
| Injection volume | 10 µL |
| Stop time | 45 min |
| INT 2 $R_t$ | 21 min |

Mobile Phase a

Preparation of the Solution

In a 1000 mL volumetric flask accurately weigh 2.0 g of ammonium acetate and then dilute to volume with water. In a 1000 mL volumetric flask transfer 600 ml of ammonium acetate solution and 300 ml of methanol. Sonicate for half an hour.

Procedure 4: HPLC Method for Monitoring the Formation and Purification of the Chelating Ligand 4.

General Procedure

The monitoring of the formation and purification of the dimeric ligand 4 were performed by reverse-phase HPLC with UV detection at 210 nm.

Analytical Conditions

| | |
| --- | --- |
| HPLC system | Liquid chromatograph Agilent 1260 Infinity |
| Stationary phase: | Synergi Polar-RP, 4 µm, 150 × 4.6 mm (Phenomenex, item 00F-4336-EO) |
| Column temperature | 40° C. |
| Mobile phase: | A: 10 mM $KH_2PO_4$<br>B: Methanol |

| Elution: Gradient | Time (min) | % B |
| --- | --- | --- |
| | 0 | 0 |
| | 5 | 0 |
| | 35 | 60 |
| | 40 | 60 |
| | 41 | 80 |
| | 46 | 80 |
| | 47 | 0 |
| | 60 | 0 |

| | |
| --- | --- |
| Flow | 0.8 mL/min |
| Detection | UV/210 nm |
| Injection volume | 10 µL |
| Stop time | 60 min |
| Compound 4 $R_t$ | 2.4 min |

Procedure 5: Determination of the Amount of Free Gadolinium Metal Ions (Free-Gd)

The determination of the amount of free gadolinium metal ions in relation to the amount of Compound 5 is performed by reverse phase HPLC (High Performance Liquid Chromatography) with FLD (Fluorescence Detector) detection. The use of EDTA (ethylenediaminetetraacetic acid) in the mobile phase ensures the formation of the Gd(EDTA) complex if free Gd(III) is present in the sample.

Chromatographic Conditions

Instrument Agilent 1100 liquid chromatograph equipped with solvent delivery system, refrigerated autosampler at 5° C., column thermostat, degasser and fluorescence detector or equivalent Column YMC-PACK ODS-AQ, 250×4.6 mm, 5 µm particle size (YMC, cod. AQ12S05-2546WT)

| | |
| --- | --- |
| Temperature: | 40° C. |
| Mobile phase: | A: $CH_3COONH_4$ (1.5 g/L), EDTA (0.55 g/L)<br>B: Methanol |
| Flow rate: | 1 mL/min |
| Detection (FLD): | wavelength excitation = 275 nm<br>wavelength emission = 314 nm |
| Run Time: | 25 min |
| Acquisition time: | 6 min |
| Injection volume: | 20 µL |
| Reference peak: | Gd(EDTA) |

| Elution: Gradient | Time (min) | % B |
| --- | --- | --- |
| | 0 | 0 |
| | 5 | 0 |
| | 10 | 50 |
| | 15 | 50 |
| | 16 | 0 |
| | 25 | 0 |

Solution Preparation

Mobile Phase

In a 1000-mL volumetric flask accurately weigh 1.5 g of ammonium acetate and dissolve with purified water, add 0.70 g of ethylenediaminetetraacetic acid disodium salt dehydrate and then dilute to volume with purified water.

Dilution Solution

In a 1000-mL volumetric flask accurately weigh 3 g of ammonium acetate and dissolve with purified water, add 1.4 g of ethylenediaminetetraacetic acid disodium salt dehydrate and then dilute to volume with purified water.

Blank Solution

Transfer 0.5 mL of purified water in vial, add 0.5 mL of dilution solution. Mix well and inject directly into the chromatographic system.

Reference Solution

In a 50 mL volumetric flask weight 0.32 g of Gadolinium acetate hydrate (expressed on the anhydrous basis, determine the water content before use) and dilute to volume with mobile phase. The concentration of Gadolinium is 3 mg/mL.

Transfer 0.1 mL of this solution in a 100 mL volumetric flask and dilute to volume with mobile phase. The concentration of Gadolinium is 0.003 mg/mL.

LOQ Solution

Transfer 1 mL of reference solution in a 5 mL volumetric flask and dilute to volume with mobile phase. The concentration of Gadolinium is 0.0006 mg/mL.

Test Solution

In a 10-mL volumetric flask accurately weight 600 mg of the sample under test (expressed on the anhydrous basis) and dilute to volume with purified water. The concentration of dimeric gadolinium complex 5 is about 60 mg/mL.

Transfer 0.5 mL of this solution in vial and add 0.5 mL of dilution solution. Mix the sample well. Once diluted immediately place the sample in the refrigerated autosampler (5-8° C.) and inject sample within 5 minutes from dilution. The final concentration of Compound 5 is about 30 mg/mL.

Analytical Sequence

Blank n=1
LOQ solution n=1
Reference solution n=6
Test solutions n=6
Reference solution n=1

System Suitability Test

Carry out the System Suitability Test (SST) every time the method is applied.

After equilibrating the chromatographic system, make one injection of the blank solution and verify the absence of interfering peaks.

Make one injection of LOQ solution

The results of the analytical sequence are valuable if the Gd(EDTA) peak has S/N ≥10.

Make six injections of the first reference solution and verify if the following requirements for the Gd(EDTA) peak are satisfied:

area repeatability of Gd(EDTA), expressed as percentage relative standard deviation (RSD %, n=6)≤10% retention time repeatability of Gd(EDTA) peak, expressed as percentage relative standard deviation (RSD %, n=6)≤2% symmetry factor, T, for Gd(EDTA) peak, calculated according to Eq. 1 0.7-2.0

$$T = w_{0.05}/2f \qquad \text{Eq. 1}$$

where:

$w_{0.05}$=width at one-twentieth of the peak height (min)
f=distance (min) between the perpendicular dropped from the peak maximum and the leading edge of the peak at one-twentieth of the peak height.

Calculation

Calculate the percentage content, Free Gd %, according to Eq. 2:

$$FreeGd\ \% = ((A_t \times W_{RS} \times (100-K) \times 20)/ \qquad \text{Eq. 2}$$
$$(A_{std} \times w \times (100-K_1) \times 50 \times 1000 \times 2.126)) \times 100$$

$A_t$=peak area of free Gd in the Test solution
$A_{std}$=Gd(EDTA) mean area in SST reference solution injections (n=6)
$W_{RS}$=mg of Gd in the reference solution
w=weight of Compound 5 sample (mg) to prepare the Test solution
K=% of $H_2O$ content in the Gadolinium acetate hydrate
$K_1$=% of $H_2O$ content in the sample
2.126=correction factor between Gadolinium acetate and Gadolinium The Limit of Quantitation for free Gd is 0.002% (w/w). Values lower than the LOQ limit should be expressed as <LOQ or n.q. (not quantifiable).

The percentage calculated as above can be converted in ppm of free-gadolinium vs. Compound 5 by multiplying such percentage*10,000.

Procedure 6: Determination of the Amount of Mono-Gadolinated Complexes (Mono-Gd)

The content of mono-Gd impurities in the dimeric complex of Compound 5 is quantified by reverse phase HPLC method in the same chromatographic run by using either FLD detector.

Quantification of specified impurity Mono-Gd (in particular, the Mono-Gd complex of ligand 4 with only one gadolinium metal ions) is done by using reference sample Mono-Gd as sodium salt by FLD detection. Mono-Gd sodium salt (reference sample) can be obtained by complexing the dimeric ligand 4 with a less then stoichiometric amount of gadolinium ions to obtain Mono-Gd, adjusting to neutral pH with NaOH and then isolating by concentration to residue.

Chromatographic Conditions

Instrument: HPLC Agilent 1100 equipped with solvent delivery system, autosampler, column thermostat, degasser, UV diode array detector and fluorescence detector 2475 Waters or equivalent

| Column: | Xselect ® HSS T3, 3.5 µm, 150 × 3.0 mm (Waters, Part No. 186004781) |
|---|---|
| Temperature: | 40° C. |
| Mobile phase: | Solvent A: Mobile phase A (40 mM Potassium Phosphate - 0.02 mM EDTA in water, pH 6.2) Solvent B: Mobile phase B (Solvent A/Acetonitrile, 60/40 v/v) |
| Flow rate: | 0.35 mL/min |
| Detection (FLD): | wavelength excitation (λex) = 275 nm wavelength emission (λem) = 314 nm |
| Detection (UV): | wavelength = 210 nm/Bw: 8 nm; Ref. wavelength = 480 nm/Bw: 80 nm |
| Run Time analysis: | 50 min |
| Acquisition time: | 32 min |
| Injection volume: | 10 µL |

| Eluition: Gradient | Time (min) | % B |
|---|---|---|
| | 0 | 0 |
| | 4 | 0 |
| | 20 | 15 |
| | 25 | 15 |
| | 30 | 100 |
| | 40 | 100 |
| | 43 | 0 |
| | 50 | 0 |

Solution Preparation

Mobile Phase A

In a 2000-mL volumetric flask accurately weigh:
8.56 g of Potassium di-hydrogen phosphate
3.97 g of Di-Potassium hydrogen phosphate tri-hydrate
0.015 g of Titriplex® III (EDTA disodium salt)

and then dilute to volume with purified water. Filter through a 0.22 μm membrane filter.

Mobile Phase B

In a 1000-mL volumetric flask transfer 600 mL of Mobile Phase A and dilute to volume with Acetonitrile. Mix well.

Solution of $CaCl_2$

In a 50-mL volumetric flask accurately weigh 165 mg of $CaCl_2$ (expressed on the anhydrous basis) and dilute to volume with purified water.

The concentration is about 3.3 mg/mL.

Stock Solution of Mono-Gd

In a 50-mL volumetric flask accurately weight 25 mg of Mono-Gd sodium salt (expressed on the anhydrous basis and purity) and dilute to volume with purified water.

The concentration of Mono-Gd is about 0.5 mg/mL.

Weight of Mono-Gd=Weight of Mono-Gd sodium salt*1140.31/1162.29

Reference Solution of Mono-Gd

In a 5-mL volumetric flask accurately transfer 0.45 mL of the stock solution of Mono-Gd. Add 1 mL of $CaCl_2$ solution and dilute to volume with purified water. The concentration of the standard is 0.045 mg/mL.

LoQ Solution of Mono-Gd

In a 5-mL volumetric flask accurately transfer 0.1 mL of the stock solution of Mono-Gd. Add 1 mL of $CaCl_2$ solution and dilute to volume with purified water. The concentration of Mono-Gd is 0.01 mg/mL.

Blank Solution

Transfer 0.8 mL of water solution in vial, add 0.2 mL of $CaCl_2$ solution. Mix well.

Test Solution

In a 5-mL volumetric flask accurately weight 125 mg of the sample under test (expressed on the anhydrous basis). Add 1 mL of $CaCl_2$ solution and dilute to volume with purified water. The concentration of Compound 5 is about 25 mg/mL.

Analytical Sequence

Blank n=1
LoQ solution n=1
Reference solution n=6
Test solutions n=6
Reference solution n=1

Calculation

Calculate the percentage content of Mono-Gd (w/w) by FLD acquisition, according to Eq. 3

$$C_{MonoGd}\% = ((A_T \times V_S \times W_S \times (100 - KF) \times a \times f)/ (A_R \times w_T \times 50 \times 100 \times (100 - KF_{Compound5}))) \times 100$$ Eq. 3 where:

$A_T$: Peak area (area sum of Mono-Gd-1/2/3/4 peaks, if present) in the Test solution $A_R$: Peak area (area sum of Mono-Gd-1/2/3/4 peaks) in the Reference solution injections (mean value n=6)

$w_T$: Weight of the sample in the Test solution (mg)

$V_S$: Volume of the Mono-Gd stock solution withdrawn to prepare the Reference solution (mL)

$W_S$: Weight of the Mono-Gd sodium salt used to prepare the stock solution (mg)

KF: % of $H_2O$ content in Mono-Gd sodium salt $KF_{Compound5}$: % of $H_2O$ content in Compound 5 a: % assay of Mono-Gd sodium salt f: correction factor for molecular weight: 0.98

The Limit of Quantitation for Mono-Gd (sum of four peaks) is 0.04% (w/w).

Values lower than the LOQ limit should be expressed as <LOQ or n.q. (not quantifiable).

The percentage calculated as above can be converted in ppm of mono-gadolinated complex vs. complex of Compound 5, by multiplying such percentage*10,000.

Example 1: Synthesis of DO3A-Tri-Tert-Butyl Ester Hydrobromide Salt

The synthesis of the starting DO3A tri-tert-butyl ester hydrobromide salt was performed by using the procedure constituting the object of the co-pending patent application EP19215900.2 (same applicant as the present application). In particular:

To a suspension of commercially available TAZA (14.39 kg; 83.53 mol) and sodium acetate (21.58 kg; 263.12 mol) in DMAC (98.07 kg; 104.33 L), a solution of tert-butyl bromoacetate (51.32 kg; 263.12 mol) in DMAC (50.72 kg; 53.96 L) was added at 10° C. during 2.5 h. Then the temperature was raised to 25° C. and the mixture was stirred for 24 h at this temperature. Water (57.56 kg) was then added in 0.5 h and after 2 h the mixture was centrifuged and washed with water (2×57 kg). The wet solid was dried under vacuum obtaining 36.62 kg; 61.48 mol of DO3A tri-tert-butyl ester hydrobromide (73.6% yield). The assay determined by HPLC (against standard) of the product is 100% w/w; the assay determined by NMR (against standard) is 99.86% w/w.

Example 2: Preparation of the Dimeric Compound 5

The dimeric complex compound 5 is obtained by using the synthetic procedure schematized below

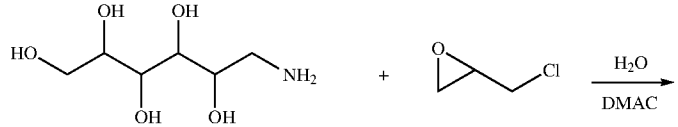

-continued
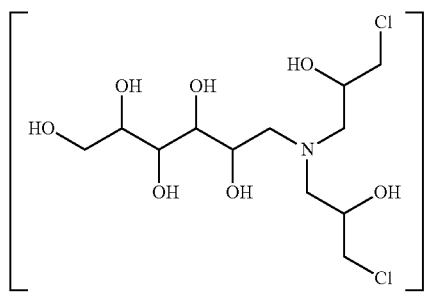 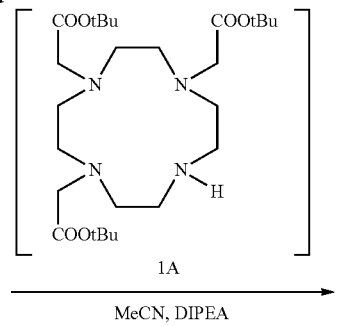
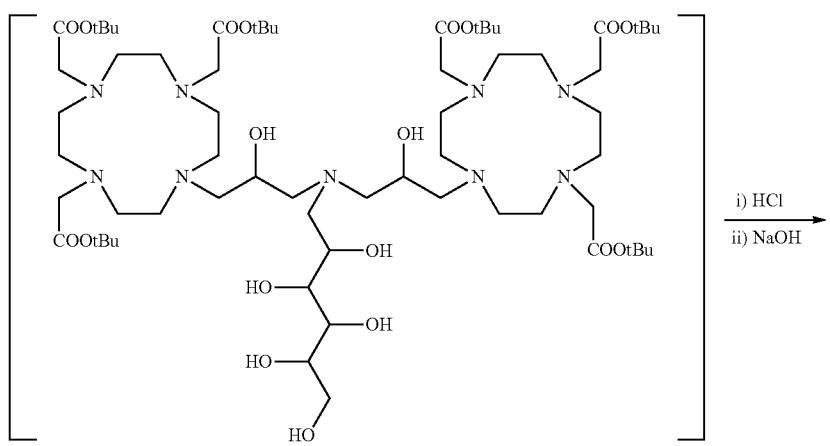
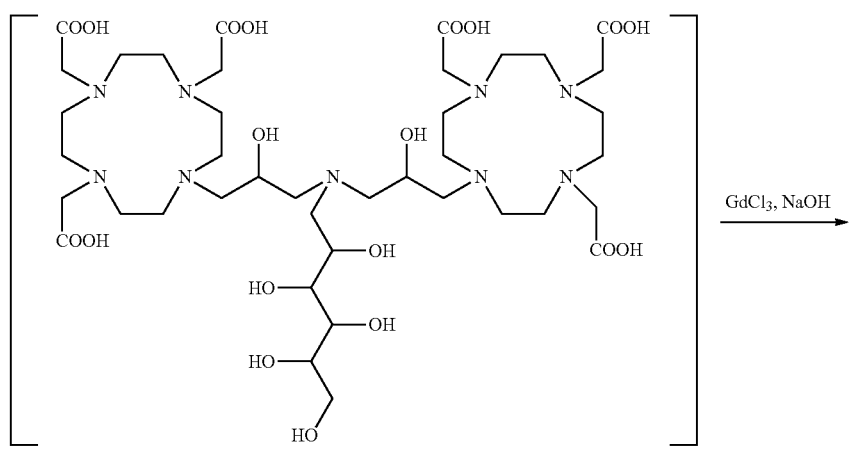

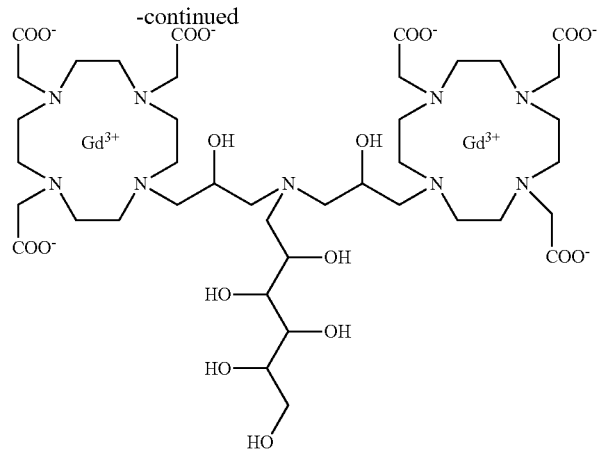

5 comprising:

a) Neutralization of the Hydrobromide to Give DO3A Tri-Tert-Butyl Ester 1A

DO3A tri-tert-butyl ester-HBr obtained as described in Example 1 (36.60 kg; 61.4 mol) and potassium carbonate (16.99 kg; 122.9 mol) are suspended in MeCN (72.50 kg; 91.77 L) at room temperature (i.e. 25° C.) and the mixture is kept under stirring for 19 h at 24° C. The resulting salts are then filtered off, and the filtrate is partially distilled at 50° C. under vacuum to give a solution of DO3A tri-tert-butyl ester 1A (31.07 kg; 60.4 mol) in MeCN with a final concentration of about 56% w/w that is used in the next step without further isolation. The 1A assay in solution is determined by an HPLC-UV method.

b) Synthesis of the Intermediate 2

D-glucamine (6 kg; 33.1 mol) in water (15.1 kg) is dropped in a solution of epichlorohydrin (6.75 kg; 73.0 mol) in DMAC (6.2 kg; 6.60 L) at room temperature in 2 h. The mixture is kept under stirring for 16 h. Then the mixture was diluted with DMAC (12.2 kg; 12.98 L) and the water is distilled at 55-60° C. under vacuum to achieve a solution of the intermediate 2 in DMAC with a residual water content <2.0% that is used for the next step without further purification.

c) Alkylation of the Intermediate 2 with DO3A Tri-Tert-Butyl Ester 1A to Give the Protected Ligand 3

DIPEA (9.80 kg; 75.8 mol) and the solution of substrate 1A collected from step a) are added to the solution of intermediate 2 heated at 50° C. and the obtained mixture is then stirred at 70° C. for 80 h by monitoring the conversion by HPLC-UV method. The mixture is then partially concentrated at 60° C. under vacuum. The residue is cooled to 25° C., diluted with a mixture of water (12.2 kg) and MeCN (19.0 kg; 24.05 L) previously prepared, and then with 25% ammonia aqueous solution (21.7 kg; 24.03 L) to give a mixture that is kept under stirring for 15 h, by obtaining the precipitation of hydrochloride salts that are filtered. The filtrate is then collected and purified by chromatography on Amberlite XAD® 1600 (450 L; eluent: gradient of water/MeCN). Then pure fractions (HPLC Area %≥90) are collected, the organic solvent is distilled, and the aqueous residue is concentrated at about 50° C. under vacuum to give a solution of the protected ligand 3 in water (conc. of about 10% w/w) suitable for use as such in the next step without any further isolation.

d) Deprotection of the Protected Ligand 3 to Give the Deprotected Ligand 4

To a mixture (219 kg) of the protected dimeric ligand 3 at a concentration of 20% (w/w), calculated on theoretical product, in water, 34% w/w hydrochloric acid aqueous solution (53.3 kg, 50.0 mol, 15 mol/mol vs protected ligand 3) is added maintaining the temperature at 30° C. At the end of the addition, the mixture is heated to 50° C. and kept under stirring for 16 h. After complete deprotection, 30% w/w sodium hydroxide aqueous solution is added until pH 5.6, and deprotected ligand 4 is obtained. The t-butanol formed as by-product is removed by distillation. The solution containing the ligand 4 is concentrated by distillation at 50° C. under vacuum until the final concentration of about 10% (w/w).

e) Complexation of the Ligand 4 to Give the Dimeric Complex 5

The solution of the dimeric ligand 4 as obtained by the previous step d) is loaded into a first reactor and heated to 40° C. Gadolinium chloride solution (2.05 mol vs. 1 mol of ligand 4) is added maintaining the temperature in the range of 37-43° C. At the end of the addition, the pH is adjusted to 5.5 by adding 10% w/w sodium hydroxide aqueous solution. The mixture is maintained at 40° C. for 3 h. A solution comprising the gadolinium complex 5 is thus obtained, and the amounts of mono-gadolinated complex (MonoGd) and free gadolinium metal ions (Free Gd) are measured. Then, the salts produced in Example 1 and in complexation steps are removed by nanofiltration; diafiltration is performed until the value of conductivity is lower than 1.0 mS/cm. At the end of the nanofiltration, the mixture is concentrated until 10÷12% w/w and 1.5 mol/mol of $Na_2HPO_4$ vs. free gadolinium metal ions (free Gd) are added to the solution. After addition of $Na_2HPO_4$, the pH of the solution is measured for each trial and is reported in Table I below (column "pH start"); formation of a white precipitate is observed. The pH is then adjusted to the value reported in Table I in the column "pH fin". The mixture is kept under stirring for 2 h. Finally, the suspension is filtered and the amounts of mono-gadolinated complex (MonoGd) and free gadolinium metal ions (Free Gd) are measured. These amounts, as well as the amounts obtained after complexation, are reported in Table I below.

TABLE I

| Trial | | Free Gd (ppm vs Compound 5) | MonoGd (ppm vs Compound 5) | pH start | pH fin |
|---|---|---|---|---|---|
| 1 | Starting | 19480 | n.q. | 7.89 | 6.13 |
|   | After filtration | 32 | n.q. | | |
| 2 | Starting | 13150 | n.q. | 7.23 | 6.10 |
|   | After filtration | 70 | n.q. | | |
| 3 | Starting | 17052 | n.q. | 6.78 | 6.08 |
|   | After filtration | 52 | n.q. | | |
| 4 | Starting | 7721 | n.q. | 7.30 | 7.30 |
|   | After filtration | 70 | n.q. | | |
| 5 | Starting | 10427 | n.q. | 7.20 | 4.90 |
|   | After filtration | 10 | n.q. | | |
| 6 | Starting | 11888 | n.q. | 6.50 | 4.54 |
|   | After filtration | 15 | 538 | | |
| 7 | Starting | 18037 | n.q. | 8.30 | 8.30 |
|   | After filtration | 250 | n.q. | | |
| 8 | Starting | 7628 | n.q. | 8.04 | 8.04 |
|   | After filtration | 318 | n.q. | | |
| 9 | Starting | 6030 | n.q. | 6.50 | 6.50 |
|   | After filtration | 75 | n.q. | | |
| 10 | Starting | 8136 | n.q. | 7.87 | 5.71 |
|    | After filtration | 24 | n.q. | | |
| 11 | Starting | 9753 | n.q. | 7.17 | 5.73 |
|    | After filtration | 60 | n.q. | | |

On basis of the results reported in Table I, it is possible to observe that there is a significant reduction of the amount of Free Gd for all trials 1 to 9 provided above. All the solutions of trials 1 to 5 and 7 to 11 contain a non-quantifiable amount of Mono-Gd, i.e. an amount of less than 400 ppm of Mono-Gd; trial 6 shows that at pH 4.54 there is an amount of MonoGd higher than the LoQ, i.e. an amount of 538 ppm vs Compound 5. Table I also shows that an amount of MonoGd <than the LoQ and low amounts of FreeGd are obtained maintaining the pH within the range of 4.9-8.3.

f) Removal of Residual Phosphates

The solutions of trial 1 obtained in the above step e) is loaded on ionic exchange resin (Diaion PA 308, previously activated) at the flow rate of 1÷3 BV/h. Removal of most of the residual phosphates from the solution is thus obtained.

g) Further Purification and Isolation of Dimeric Gadolinium Complex

The solution of the above step f) is loaded in a second reactor, the pH of the solution is adjusted to 5.7÷6.3 by diluted HCl addition, and water is distilled at 45÷55° C. under vacuum until the assay of the gadolinium complex is about 20÷25% w/w. The concentrated solution is loaded with a flow rate of 0.5 BV/h on Amberlite XAD® 1600 (amount of resin: 30 mL/g of product), previously activated. The purification is performed with water and mixture of isopropanol and water.

The fractions with high purity (evaluation on HPLC-FLD/UV) are loaded into another reactor. After preliminary concentration a treatment with carbon is performed. The suspension is filtered in order to remove the carbon and the solution is concentrated under vacuum at 45÷55° C. until 25% w/w concentration, from which the gadolinium complex is isolated by spray drying as a white powder solid (14.1 kg, 12.7 kg on anhydrous base, 9.83 mol) with a final titration assay of 99% (w/w %; on anhydrous base).

Overall yield determined from DO3A tri-tert-butyl ester 1A: 33%.

Example 3: Further Trials of Precipitation with Precipitating Agents

Trial 12

To a 10% w/w solution of complex 5 containing free gadolinium as obtained by the procedure of steps a) to d) of Example 2 above, the content of mono-gadolinated complex (MonoGd) and free gadolinium metal ions (FreeGd) are measured. Then, $K_3PO_4$ is added (1.5 mol vs mol of free Gd) to the solution.

After phosphate addition, the pH rises from 5.42 until 9.00 and formation of a white solid is immediately observed. The mixture is maintained at pH 9.00 under stirring for 2 h at rT and, then, the solid is filtered obtaining a solution. The content of free gadolinium metal ions (Free Gd) and mono-gadolinated complex (MonoGd) is measured and reported in Table II below.

TABLE II

| Trial | Free Gd ppm vs Compound 5 | MonoGd ppm vs Compound 5 |
|---|---|---|
| Starting | 13744 | n.q. |
| After filtration | 136 | n.q. |

On basis of the results reported in Table II, it is possible to observe that, with the precipitation with phosphate as a precipitating agent, there is a significant reduction of the amount of Free Gd. Moreover, the solution contains a non-quantifiable amount of Mono-Gd, i.e. an amount of less than 400 ppm of Mono-Gd.

Trial 13

To a 10% w/w solution of complex 5 containing free gadolinium as obtained by the procedure of steps a) to d) of Example 2 above, the content of mono-gadolinated complex (MonoGd) and free gadolinium metal ions (FreeGd) are measured. Then, disodium oxalate is added (2.25 mol/mol vs free Gd) to the solution.

After oxalate addition, the pH rises from 5.56 until 7.78 and formation of a white solid is immediately observed. The pH is then reduced until 6.43 with HCl 1N. At the end the mixture is maintained at room temperature for 2 h.

After the suspension is filtered, the content of mono-gadolinated complex and free gadolinium metal ions are measured. The content of mono-gadolinated complex (MonoGd) and of free gadolinium metal ions (Free Gd) are reported in Table III below.

TABLE III

| Trial | Free Gd ppm vs Compound 5 | MonoGd ppm vs Compound 5 |
|---|---|---|
| Starting | 11730 | n.d. |
| After filtration | 64 | n.q. |

Table III clearly shows that carrying out a trial as above, and in particular a trial involving oxalate as a precipitating agent in suitable amounts, provides a solution comprising very low amounts of Free Gd and an amount of MonoGd below the LoQ.

The invention claimed is:

1. A process for the manufacturing of a dimeric complex compound 5 of formula

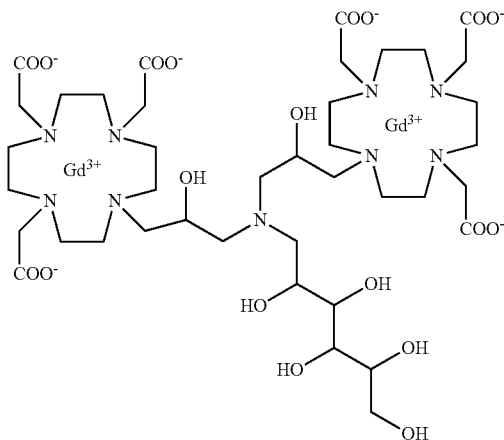

which comprises:

1) Preparing a solution of DO3A tri-tert-butyl ester of formula 1A

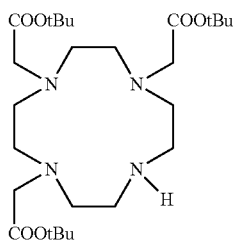

in an organic solvent;

2) Preparing a solution of a compound of formula 2

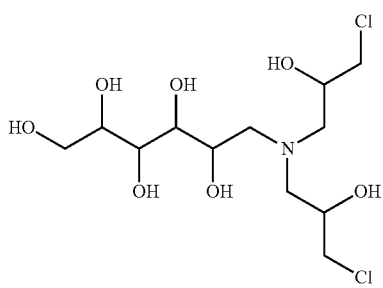

in an organic solvent;

3) Admixing the solutions prepared according to steps 1) and 2) to obtain a solution of a compound of formula 3

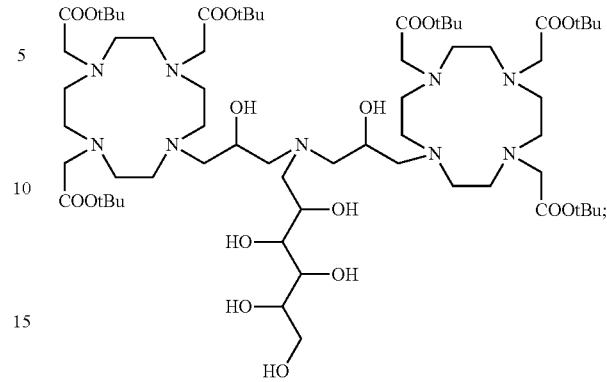

4) Without isolating the compound from the solution of step 3), removing the tert-butyl protecting groups from the compound of formula 3 to obtain a solution of a respective free ligand of formula 4

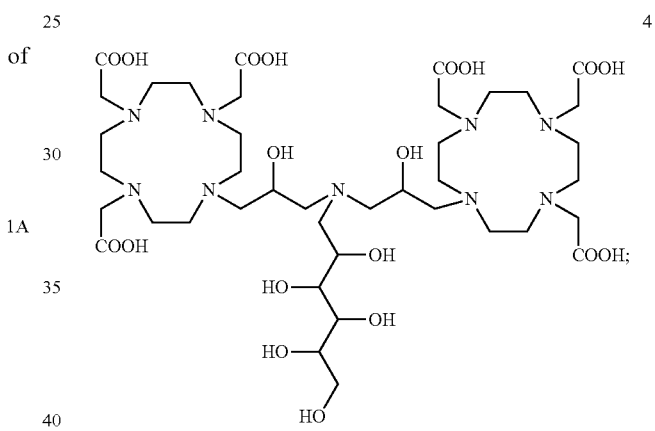

5) Without isolating the free ligand of formula 4, adding a molar excess of gadolinium metal ions to the solution of step 4) in an amount of 2.05 moles or more with respect to 1 mole of deprotected dimeric ligand of formula 4 to obtain a solution of the respective dimeric complex of formula 5;

6) Adding to the solution of the dimeric complex of formula 5 a precipitating agent to precipitate a portion of free gadolinium metal ions; and 7) isolating the dimeric complex of formula 5 as a white solid by spray drying of the solution directly collected from step 6), wherein a reaction solvent in all the steps following the preparation of the compound of formula 3 is an aqueous solvent.

2. The process of claim 1 wherein the solution of the DO3A tri-tert-butyl ester 1A of step 1) is prepared from a hydrobromide salt of the DO3A tri-tert-butyl ester.

3. The process of claim 1 wherein step 1) comprises:
   i) suspending a hydrobromide salt of the DO3A tri-tert-butyl ester together with a base or a basic salt in an organic solvent to obtain a suspension;
   ii) filtering the suspension; and
   iii) collecting and optionally concentrating the filtered suspension, to obtain a solution of the DO3A tri-tert-butyl ester 1A in the organic solvent.

4. The process of claim 1 wherein step 2) comprises reacting D-glucamine with epichlorohydrin, to obtain a solution of the compound of formula 2 in an organic solvent, comprising the following steps:
   i) adding an aqueous solution of D-glucamine to a solution of epichlorohydrin in an organic solvent, to give the compound of formula 2 in a water/organic solvent mixture; and
   ii) removing the water from the mixture, to obtain a solution of the compound of formula 2 in the organic solvent.

5. The process of claim 4 wherein the organic solvent is Dimethylacetamide (DMAC).

6. The process of claim 1, wherein step 3) comprises
   a. reacting the compound of formula 2 from step 2) with DO3A tri-tert-butyl ester 1A from step 1) in the presence of a base to give an organic crude solution;
   b. diluting the obtained organic crude solution with water, a water/organic solvent mixture, or an aqueous solution to obtain a water/organic crude;
   c. purifying by distillation the water/organic crude, to obtain the compound of formula 3 in a water/organic solvent mixture, and
   d. removing the organic solvent from the mixture to obtain an aqueous solution of the compound of formula 3.

7. The process of claim 1, wherein step 4) comprises:
   i) adding an acid to the aqueous solution of the compound of formula 3 from step 3), then and/or during such addition, heating and/or maintaining the temperature of the solution to a temperature higher than 40° C. to remove the protecting tert-butyl groups and obtain an acidic aqueous solution of the respective free ligand of formula 4;
   ii) adding a base to the acidic solution to obtain a substantially neutral aqueous solution of the free ligand;
   iii) purifying by distillation and then optionally concentrating the obtained neutral solution to obtain an aqueous solution of the free ligand of formula 4.

8. The process of claim 7 wherein step iii) comprises: distilling the neutral solution for removing a formed t-butanol; and optionally concentrating the aqueous solution.

9. The process of claim 1, wherein during and/or after the addition of the precipitating agent according to step 6), the pH is adjusted to and/or maintained at a value of 4.5 or higher.

10. The process of claim 9, wherein during and/or after the addition of the precipitating agent according to step 6), the pH is adjusted to and/or maintained at a value of 4.7 or higher.

11. The process of claim 10, wherein during and/or after the addition of the precipitating agent according to step 6), the pH is adjusted to and/or maintained at a value of 4.9 or higher.

12. The process of claim 11, wherein during and/or after the addition of the precipitating agent according to step 6), the pH is adjusted to and/or maintained at a value of 5.5 or higher.

13. The process of claim 1, wherein the precipitating agent is added in an amount from 1.1 to 5 moles, with respect to 1 mole of gadolinium metal ions within the solution of the dimeric complex of formula 5 obtained from step 5).

14. The process of claim 13, wherein the precipitating agent is added in an amount from 1.2 to 3 moles, with respect to 1 mole of gadolinium metal ions within the solution of the dimeric complex of formula 5 obtained from step 5).

15. The process of claim 14, wherein the precipitating agent is added in an amount from 1.4 to 2.5 moles, with respect to 1 mole of gadolinium metal ions within the solution of the dimeric complex of formula 5 obtained from step 5).

16. The process of claim 15, wherein the precipitating agent is added in an amount from 1.4 to 1.6 moles, with respect to 1 mole of gadolinium metal ions within the solution of the dimeric complex of formula 5 obtained from step 5).

17. The process of claim 1, wherein the precipitating agent is at least one selected from the group consisting of phosphate ($PO_4^{3-}$), monohydrogen phosphate ($HPO_4^{2-}$), dihydrogen phosphate ($H_2PO_4^-$), orthophosphoric acid ($H_3PO_4$), oxalate ($C_2O_4^{2-}$), hydrogen oxalate ($HC_2O_4^-$), and oxalic acid ($H_2C_2O_4$).

18. The process of claim 1, wherein after step 6) and before step 7), the process further comprises the step of filtering the obtained solution of gadolinium complex 5 after addition of the precipitating agent to remove the precipitated insoluble gadolinium salt from said solution.

19. The process of claim 4, wherein the amount of epichlorohydrin is in an excess over the stoichiometric amount.

20. The process of claim 7, wherein the acid is an inorganic acid comprising a counterion having a single negative charge.

21. The process of claim 7, wherein the temperature is higher than 40° C. and up to 60° C.

22. A process for the manufacturing of a dimeric complex compound 5 of formula

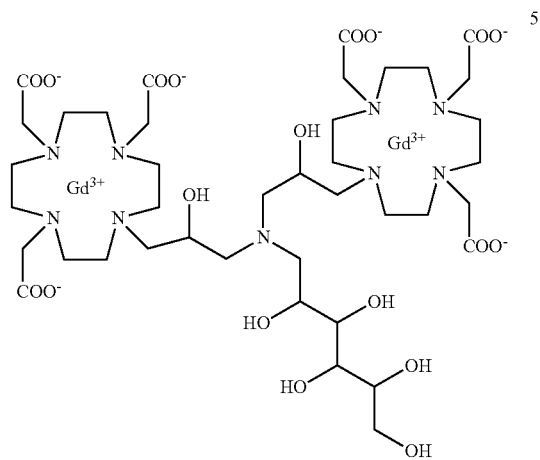

which comprises:
1) Preparing a solution of DO3A tri-tert-butyl ester of formula 1A

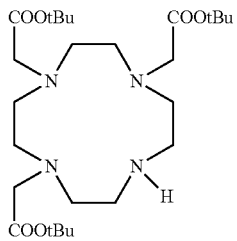

in an organic solvent;
2) Preparing a solution of a compound of formula 2

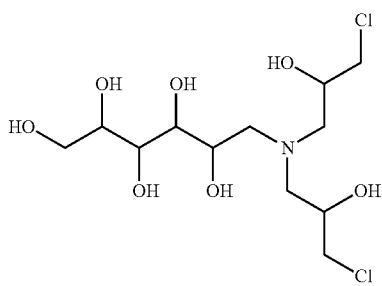

in an organic solvent;
3) Admixing the solutions prepared according to steps 1) and 2) to obtain a solution of a compound of formula 3

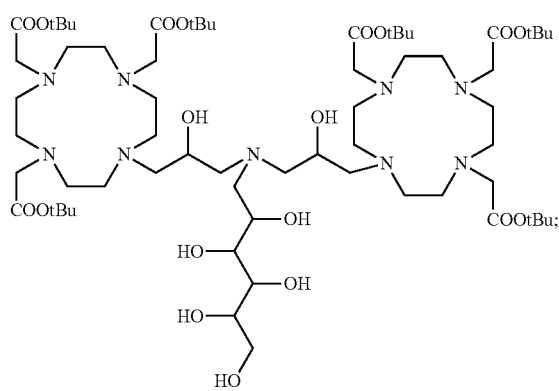

4) Without isolating the compound from the solution of step 3), removing the tert-butyl protecting groups from the compound of formula 3 to obtain a solution of a respective free ligand of formula 4

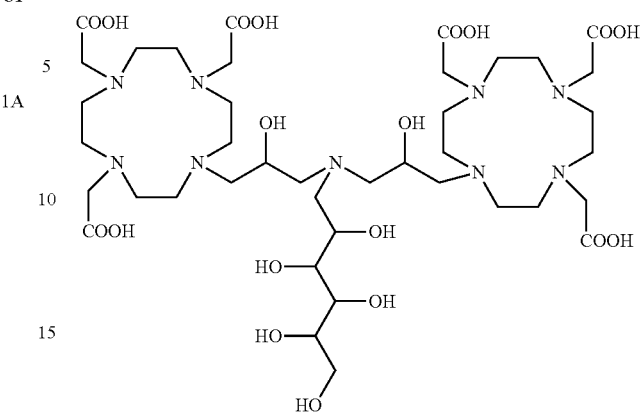

by:
i) adding an inorganic acid comprising a counterion having a single negative charge to the aqueous solution of the compound of formula 3 from step 3), then and/or during such addition, heating and/or maintaining the temperature of the solution to a temperature higher than 40° C. to remove the protecting tert-butyl groups and obtain an acidic aqueous solution of the respective free ligand of formula 4;
ii) adding a base to the acidic solution to obtain a substantially neutral aqueous solution of the free ligand;
iii) purifying by distillation and then optionally concentrating the obtained neutral solution to obtain an aqueous solution of the free ligand of formula 4;
5) Without isolating the free ligand of formula 4, adding a molar excess of gadolinium metal ions to the solution of step 4) in an amount of 2.05 moles or more with respect to 1 mole of deprotected dimeric ligand of formula 4 to obtain a solution of the respective dimeric complex of formula 5;
6) Adding to the solution of the dimeric complex of formula 5 a precipitating agent to precipitate a portion of free gadolinium metal ions; and
7) isolating the dimeric complex,
wherein a reaction solvent in all the steps following the preparation of the compound of formula 3 is an aqueous solvent.

23. The process of claim 22 wherein the solution of the DO3A tri-tert-butyl ester 1A of step 1) is prepared from a hydrobromide salt of the DO3A tri-tert-butyl ester.

24. The process of claim 22 wherein step 1) comprises:
i) suspending a hydrobromide salt of the DO3A tri-tert-butyl ester together with a base or a basic salt in an organic solvent to obtain a suspension;
ii) filtering the suspension; and
iii) collecting and optionally concentrating the filtered suspension, to obtain a solution of the DO3A tri-tert-butyl ester 1A in the organic solvent.

25. The process of claim 22 wherein step 2) comprises reacting D-glucamine with epichlorohydrin, to obtain a solution of the compound of formula 2 in an organic solvent, comprising the following steps:
i) adding an aqueous solution of D-glucamine to a solution of epichlorohydrin in an organic solvent, to give the compound of formula 2 in a water/organic solvent mixture; and ii) removing the water from the mixture, to obtain a solution of the compound of formula 2 in the organic solvent.

26. The process of claim 25 wherein the organic solvent is Dimethylacetamide (DMAC).

27. The process of claim 22, wherein step 3) comprises
    a. reacting the compound of formula 2 from step 2) with DO3A tri-tert-butyl ester 1A from step 1) in the presence of a base to give an organic crude solution;
    b. diluting the obtained organic crude solution with water, a water/organic solvent mixture, or an aqueous solution to obtain a water/organic crude;
    c. purifying by distillation the water/organic crude, to obtain the compound of formula 3 in a water/organic solvent mixture, and
    d. removing the organic solvent from the mixture to obtain an aqueous solution of the compound of formula 3.

28. The process of claim 22 wherein step iii) comprises: distilling the neutral solution for removing a formed t-butanol; and optionally concentrating the aqueous solution.

29. The process of claim 22, wherein in step 5), gadolinium metal ions are added to the solution of step 4) in an amount of 2.05 moles or more with respect to 1 mole of deprotected dimeric ligand of formula 4.

30. The process of claim 22, wherein during and/or after the addition of the precipitating agent according to step 6), the pH is adjusted to and/or maintained at a value of 4.5 or higher.

31. The process of claim 30, wherein during and/or after the addition of the precipitating agent according to step 6), the pH is adjusted to and/or maintained at a value of 4.7 or higher.

32. The process of claim 31, wherein during and/or after the addition of the precipitating agent according to step 6), the pH is adjusted to and/or maintained at a value of 4.9 or higher.

33. The process of claim 32, wherein during and/or after the addition of the precipitating agent according to step 6), the pH is adjusted to and/or maintained at a value of 5.5 or higher.

34. The process of claim 22, wherein the precipitating agent is added in an amount from 1.1 to 5 moles, with respect to 1 mole of gadolinium metal ions within the solution of the dimeric complex of formula 5 obtained from step 5).

35. The process of claim 34, wherein the precipitating agent is added in an amount from 1.2 to 3 moles, with respect to 1 mole of gadolinium metal ions within the solution of the dimeric complex of formula 5 obtained from step 5).

36. The process of claim 35, wherein the precipitating agent is added in an amount from 1.4 to 2.5 moles, with respect to 1 mole of gadolinium metal ions within the solution of the dimeric complex of formula 5 obtained from step 5).

37. The process of claim 36, wherein the precipitating agent is added in an amount from 1.4 to 1.6 moles, with respect to 1 mole of gadolinium metal ions within the solution of the dimeric complex of formula 5 obtained from step 5).

38. The process of claim 22, wherein the precipitating agent is at least one selected from the group consisting of phosphate ($PO_4^{3-}$), monohydrogen phosphate ($HPO_4^{2-}$), dihydrogen phosphate ($H_2PO_4^-$), orthophosphoric acid ($H_3PO_4$), oxalate ($C_2O_4^{2-}$), hydrogen oxalate ($HC_2O_4^-$), and oxalic acid ($H_2C_2O_4$).

39. The process of claim 22, wherein after step 6) and before step 7), the process further comprises the step of filtering the obtained solution of gadolinium complex 5 after addition of the precipitating agent to remove the precipitated insoluble gadolinium salt from said solution.

40. The process of claim 22 wherein step 7) comprises isolating the dimeric complex of formula 5 as a white solid by spray drying of the solution directly collected from step 6).

41. The process of claim 25, wherein the amount of epichlorohydrin is in an excess over the stoichiometric amount.

42. The process of claim 22, wherein the temperature is higher than 40° C. and up to 60° C.

* * * * *